(12) United States Patent
Narasimhan et al.

(10) Patent No.: US 10,874,737 B2
(45) Date of Patent: Dec. 29, 2020

(54) INFLUENZA NANOVACCINE

(71) Applicants: Iowa State University Research Foundation, Inc., Ames, IA (US); University of Iowa Research Foundation, Iowa City, IA (US)

(72) Inventors: Balaji Narasimhan, Ames, IA (US); Kathleen A. Ross, Ames, IA (US); Kevin L. Legge, Iowa City, IA (US); Thomas J. Waldschmidt, Iowa City, IA (US)

(73) Assignees: Iowa State University Research Foundation, Inc., Ames, IA (US); University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 16/370,444

(22) Filed: Mar. 29, 2019

(65) Prior Publication Data
US 2019/0365887 A1 Dec. 5, 2019

Related U.S. Application Data

(60) Provisional application No. 62/681,447, filed on Jun. 6, 2018, provisional application No. 62/679,330, filed on Jun. 1, 2018.

(51) Int. Cl.
| | |
|---|---|
| *A61K 39/39* | (2006.01) |
| *A61P 31/16* | (2006.01) |
| *A61K 9/14* | (2006.01) |
| *A61K 39/145* | (2006.01) |
| *A61K 9/51* | (2006.01) |
| *A61K 39/00* | (2006.01) |

(52) U.S. Cl.
CPC ............... *A61K 39/39* (2013.01); *A61K 9/14* (2013.01); *A61K 9/51* (2013.01); *A61K 39/145* (2013.01); *A61P 31/16* (2018.01); *A61K 2039/525* (2013.01); *A61K 2039/6093* (2013.01)

(58) Field of Classification Search
None
See application file for complete search history.

(56) References Cited

U.S. PATENT DOCUMENTS

| | | |
|---|---|---|
| 5,762,939 A | 6/1998 | Smith et al. |
| 6,475,995 B1 | 11/2002 | Roy et al. |
| 7,285,289 B2 | 10/2007 | Nagy et al. |
| 2008/0160089 A1 | 7/2008 | Vitiello et al. |
| 2010/0285135 A1 | 11/2010 | Wendorf et al. |
| 2018/0243228 A1 | 8/2018 | Gourapura et al. |

OTHER PUBLICATIONS

Lauster et al., Multivalent Peptide—Nanoparticle Conjugates for Influenza-Virus Inhibition, 2017, Angew. Chem. Int. Ed., vol. 56, pp. 5931-5936.*
Hu et al., Multi-antigen avian influenza a (H7N9) virus-like particles: particulate characterizations and immunogenicity evaluation in murine and avian models, 2017, BMC Biotechnology, vol. 17, No. 2, pp. 1-12.*
Wafa et al., The Effect of Polyanhydride Chemistry in Particle-based Cancer Vaccines on the Magnitude of the Antitumor Immune Response, 2017, Acta Biomater., vol. 50, pp. 417-427.*
Ross et al., Structural and antigenic stability of H5N1 hemagglutinin trimer upon release from polyanhydride nanoparticles, 2014, Journal Biomed Mater Res Part A, vol. 102A, pp. 4161-4168.*
Goodman et al., "Adaptive Immunity and Protection Generated by Nanoparticle-based Vaccination against Influenza Virus," Front. Bioeng. Biotechnol. Conference Abstract: 10th World Biomaterials Congress, Montréal, Canada, May 17-May 22, 2016, 2pgs.
Haughney et al., "Effect of Nanovaccine Chemistry on Humoral Immune Response Kinetics and Maturation," Nanoscale, 6(22):13770-13778, Nov. 2014.
Kim et al., "Antigen Persistence and the Control of Local T Cell Memory by Migrant Respiratory Dendritic Cells After Acute Virus Infection," J Exp Med., 207(6):1161-1172, Jun. 2010.
Kipper et al., "Single Dose Vaccine Based on Biodegradable Polyanhydride Microspheres Can Modulate Immune Response Mechanism," J Biomed Mater Res A., 76(4):798-810, Mar. 2006.
Narasimhan, B., "Pathogen Mimicking Nanovaccine Platform Technology: A New Paradigm," Nat'l Univ of Singapore, Department of Microbiology & Immunology Programme Seminar Series, Aug. 15, 2013, 1 pg.
Plotkin, S.A., "Vaccines: Correlates of Vaccine-Induced Immunity," Clin Infect Dis., 47(3):401-409, Aug. 2008.
Ross et a., "Combination Nanovaccine Demonstrates Synergistic Enhancement in Efficacy against Influenza," ACS Biomater. Sci. Eng., 2(3):368-374, Jan. 2016.
Ross et al., "Hemagglutinin-Based Polyanhydride Nanovaccines against H5N1 Influenza Elicit Protective Virus Neutralizing Titers and Cell-Mediated Immunity," Int J Nanomedicine, 10:229-243, Dec. 2014.
Ross et al., "(526e) Intranasal Nanovaccine Provides Protection Against Homologous and Heterologous Influenza Virus," accessed on the internet at https://www.aiche.org/conferences/aiche-annual-meeting/2017/proceeding/paper/526e-intranasal-nanovaccine-provides-protection-against-homologous-and-heterologous-influenza-virus, retrieved Mar. 30, 2018, 3pgs.
Ross, K., "Synthetic Nanoparticle-based Vaccines against Respiratory Pathogens," Iowa State University, Dissertation, 2013.
Torres et al., "Synthesis and Characterization of Novel Polyanhydrides with Tailored Erosion Mechanisms," J Biomed Mater Res A., 76(1):102-110, Jan. 2006.

(Continued)

*Primary Examiner* — Benjamin P Blumel
(74) *Attorney, Agent, or Firm* — Haukaas Fortius PLLC; Michael H. Haukaas

(57) ABSTRACT

Immunogenic compositions and methods of using them include a biodegradable or bioerodible polyanhydride nanoparticle comprising 1,8-bis(p-carboxyphenoxy)-3,6-dioxaoctane (CPTEG) and 1,6-bis(p-carboxyphenoxy)hexane (CPH) copolymers, an immunogenic protein of an Influenza Virus and an adjuvant entrapped within an interior of the nanoparticle, and an excipient. The immunogenic composition may be administered to a subject to confer both local and systemic immunity to the Influenza Virus.

20 Claims, 24 Drawing Sheets

(56) References Cited

OTHER PUBLICATIONS

Ulery et al., "Design of a Protective Single-Dose Intranasal Nanoparticle-Based Vaccine Platform for Respiratory Infectious Diseases," PLoS One, 6(3):e17642, Mar. 2011.
Van De Sandt et al., "Differential Recognition of Influenza A Viruses by M158-66 Epitope-Specific CD8+T Cells is Determined by Extraepitopic Amino Acid Residues," J Virol., 90(2):1009-1022, Nov. 2015.
Vela Ramirez et al., "Polyanhydride Nanovaccines Induce Germinal Center B Cell Formation and Sustained Serum Antibody Responses," J Biomed Nanotechnol., 12(6):1303-1311, Jun. 2016.
Zacharias et al., "Polyanhydride Nanovaccine Induces Robust Pulmonary B and T Cell Immunity and Confers Protection Against Homologous and Heterologous Influenza A Virus Infections," Front. Immunol., 9(1953):14, Aug. 2018.

\* cited by examiner

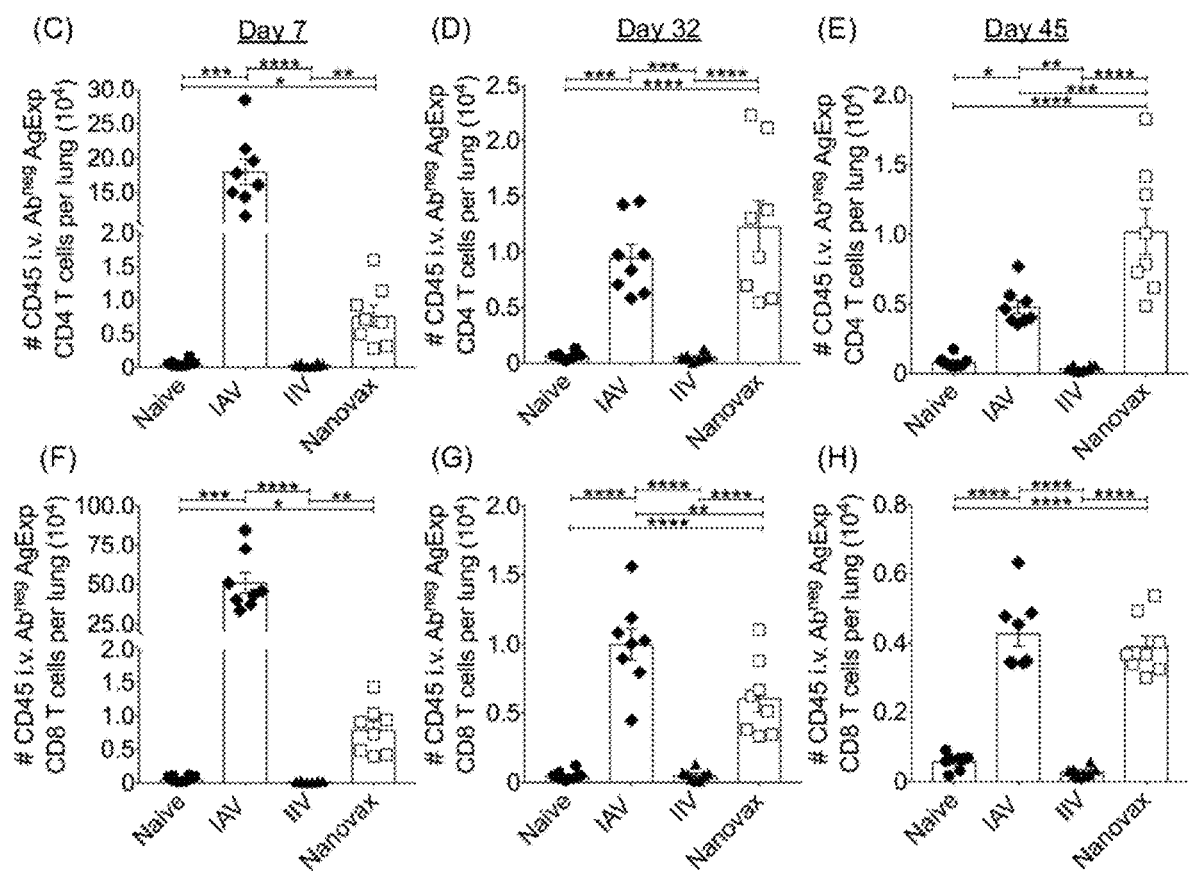
*Fig. 3 (con't.)*

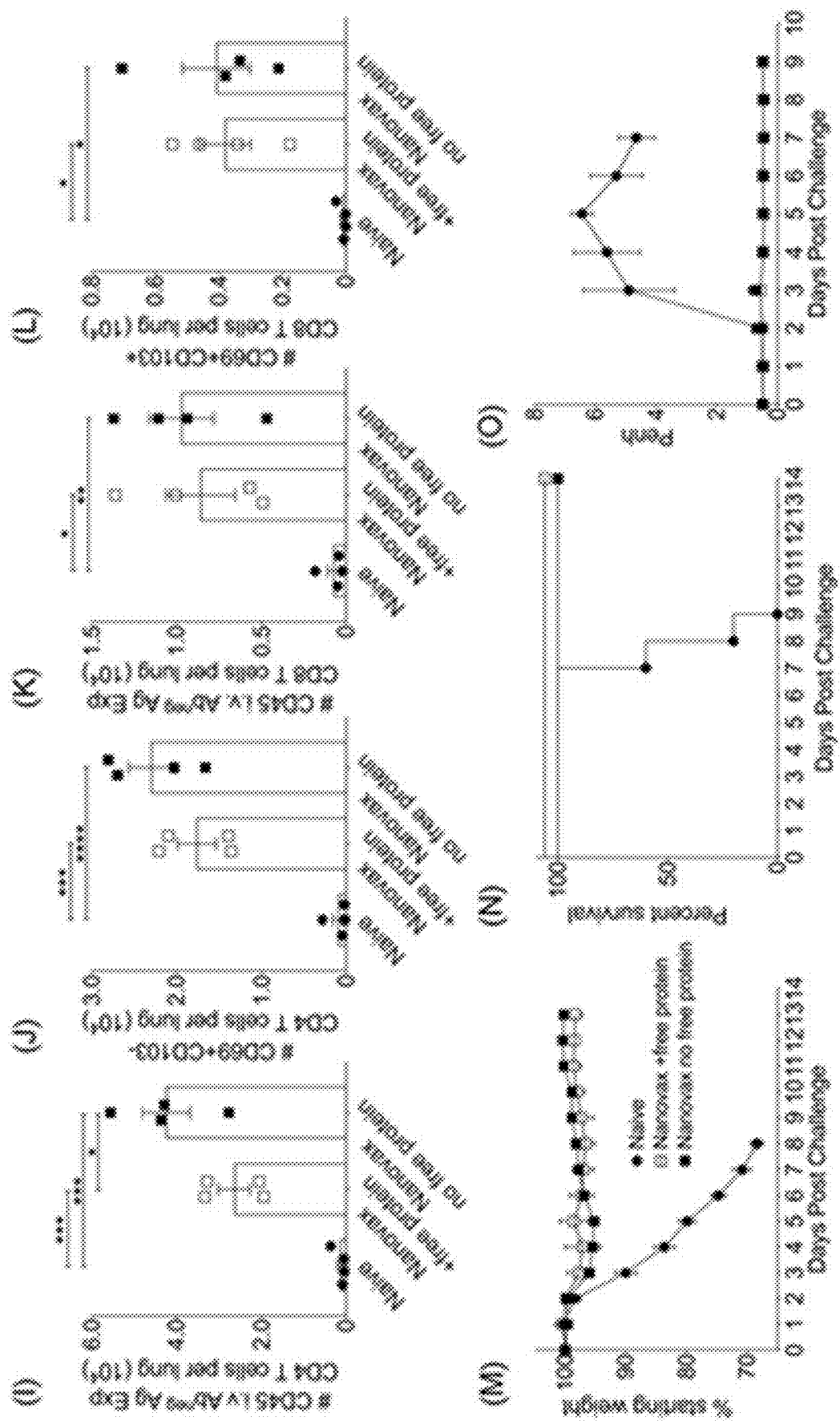
Fig. 11 (con't.)

INFLUENZA NANOVACCINE

RELATED APPLICATION

This application claims priority under 35 U.S.C. § 119(e) to U.S. Provisional Patent Application Nos. 62/679,330 filed Jun. 1, 2018 and 62/681,447 filed Jun. 6, 2018, which applications are incorporated herein by reference.

GOVERNMENT SUPPORT

This invention was made with government support under Grant No. R01 AI127565 awarded by the National Institutes of Health. The government has certain rights in the invention.

FIELD OF INVENTION

The present invention relates generally to immunogenic compositions, and more particularly, to an immunogenic composition that may confer protective immunity to a subject against an influenza virus.

BACKGROUND OF THE INVENTION

The influenza virus is an RNA enveloped virus with a particle size of about 125 nm in diameter. The virus generally comprises an internal nucleocapsid or core of ribonucleic acid (RNA) associated with nucleoprotein, surrounded by a viral envelope with a lipid bilayer structure and external glycoproteins. The inner layer of the viral envelope is predominantly composed of matrix proteins and the outer layer mostly composed of host-derived lipid material. The surface glycoproteins neuraminidase (NA) and hemagglutinin (HA) appear as outward radiating appendages or spikes, 10 to 12 nm long, from the surface of the virus particles. These surface proteins, and in particular the hemagglutinin protein, may be used to determine the antigenic specificity of the influenza subtypes.

The influenza family of viruses may be categorized into four serotypes types: A, B, C and D. Influenza A and B viruses cause seasonal epidemics of disease almost every winter in the United States. Influenza type C infections generally cause a mild respiratory illness and are not thought to cause epidemics. The Influenza D viruses primarily affect cattle and are not known to infect or cause illness in people.

Influenza A virus (IAV) may be further categorized according to subtypes based on the variant of hemagglutinin and the neuraminidase expressed on the viral surface. There are 18 different hemagglutinin subtypes (H1-H18) and 11 different neuraminidase subtypes (N1-N11), and each subtype may be further classified into various strains according to the HA an N subtype (e.g., H1N1, H3N1, etc.).

IAV is a common respiratory pathogen that undergoes seasonal antigenic drift continually giving rise to variant strains that may escape existing immune protection. This viral drift detrimentally impacts public health as well as the economy within the United States. For example, during the 2015-2016 flu season, IAV caused approximately 310,000 hospitalizations, 12,000 deaths, and incurred $87 million-dollars in financial burden. Each of these burdens may be exacerbated during years when an antigenic shift event gives rise to pandemic strains further underscoring the need to thwart the spread of IAV.

The most effective way to deal with the influenza virus for the population most at risk of severe complications is through infection prevention. For example, use of an available influenza vaccine is an effective way to lower the mortality rate in a population. However due to the ever-changing nature of the influenza virus, the development of an effective vaccine to protect against the currently circulating virus strains is complex and expensive. Moreover, patient compliance in receiving the vaccine is generally very low. Thus, large numbers of patients at risk of serious complications from influenza virus go unprotected.

Traditional vaccination strategies that have been used to prevent the spread of IAV primarily includes two vaccines: inactivated influenza vaccine (IIV) and live-attenuated influenza vaccine (LAIV). In the 2015-2016 IAV season, IIV and LAIV were estimated to avert 5 million IAV-induced illnesses and 3,000 deaths within the United States alone.

Both IIV and LAIV largely prevent IAV infection by inducing the production of neutralizing antibodies; however, each of the vaccines induce distinctive immune responses due, at least in part, to their disparate formulations and inoculation routes. IIV contains inactivated IAV proteins/virus in the presence or absence of a variety of adjuvants and is administered intramuscularly (i.m.). In contrast, LAIV utilizes a temperature-sensitive attenuated strain of IAV that is given intranasally (i.n.) as a needle-free spray. Despite these differences, both IIV and LAIV provide systemic immunity by inducing IAV-specific antibody (humoral) responses. However, it is less clear if these vaccination strategies generate robust IAV-specific CD4 or CD8 T cell responses, the latter requiring presentation of viral antigens via either direct infection of antigen presenting cells (APC) or cross-presentation. Furthermore, due to its i.m. delivery, IIV is not thought to drive airway-resident effector T cell responses as the nasal mucosa and the lungs are not directly involved in any vaccine induced priming of naive T cells. In contrast, while LAIV is capable of replicating and may induce effector T cell immunity in the upper airway, LAIV is unable to produce local immunity in the lower airway. Thus, even when de novo T cell responses are generated by IIV or LAIV, the tissue localization of these responses suggests that neither would drive long-term T cell memory within the lung airways.

Additionally, recommendations in recent years against the use of LAIV by the Centers for Disease Control and Prevention due to its reduced effectiveness indicates that in some years there is no currently approved vaccine that is needle-free or that induces even limited local immunity within the airways. These vaccine limitations—in combination with IAV disease burden—have resulted in increased efforts in developing innovative IAV vaccination strategies that generate systemic and local immunity within the upper and lower airways of the lungs.

Accordingly, a need exists for an easily administered and low dose immunogenic composition capable of producing a humoral and cell-mediated immunogenic response that is both systemic and tissue specific. The present invention satisfies this need.

SUMMARY OF THE INVENTION

The invention provides for immunogenic compositions and methods of use that generally include a biodegradable polyanhydride nanoparticle comprising one or more influenza virus immunogenic proteins and an adjuvant each entrapped within the interior of the nanoparticle.

In certain preferred embodiments of the invention, the immunogenic composition may comprise at least a first biodegradable polyanhydride nanoparticle formed of 1,8-bis (p-carboxyphenoxy)-3,6-dioxaoctane (CPTEG) and 1,6-bis (p-carboxyphenoxy) hexane (CPH) copolymers in a ratio of about 20:80, an immunogenic protein or proteins of Influenza A Virus, Influenza B Virus, Influenza C Virus, or Influenza D Virus, and an adjuvant, each of the immunogenic proteins and adjuvant entrapped within an interior of the nanoparticle, and an excipient.

Other preferred immunogenic compositions include at least a second biodegradable polyanhydride nanoparticle having at least a second immunogenic protein of an Influenza Virus and an adjuvant within an interior of the second nanoparticle. However, the second immunogenic protein(s) may be different than the immunogenic protein(s) in the first nanoparticle.

Preferably, the immunogenic protein includes one or more of Hemagglutinin (HA), Neuraminidase (NA), Nucleocapsid Protein (NP), Matrix Protein 1 (M1), Matrix Protein 2 (M2), Polymerase Basic Protein 1 (PB1), Polymerase Basic Protein 2 (PB2), Polymerase Acidic Protein (PA), Nonstructural Proteins 1 (NS1), Nonstructural Proteins 2/Nuclear Export Protein (NS2/NEP), Polymerase Basic Protein 1 Segment Second Proteins (PB1-F2), Influenza B Virus Membrane Protein (BM2), Influenza B Virus Membrane Protein (NB), Influenza A Virus Segment 2 Alternative Splicing Protein (M42), Influenza A Virus Segment 1 Alternative Splicing Protein (PB2-S1), Influenza A Virus Segment 2 Alternative Initiation Protein (N40), Influenza A Virus Segment 3Ribosomal Shift Protein (PA-X), Influenza A Virus Segment 3 Alternative Initiation Protein (PA-N182), Influenza A Virus Segment 3 Alternative Initiation Protein (PA-N155), Influenza C/D Virus Polymerase Complex Protein (P3), Influenza C/D Virus Surface Glycoproteins: Hemagglutinin, Esterase, and Fusion activities (HEF), Influenza C/D Virus Matrix Protein (CM1), or Influenza C/D Virus surface glycoprotein CM2.

Certain embodiments of the invention include one or more immunogenic proteins of an Influenza A virus subtype H1, H2, H3, H5, and H7. In other preferred embodiments, the immunogenic proteins may include one or more of Influenza A Virus HA subtypes H1 and H3; Influenza A Virus NA subtypes N1 and N2; Influenza A Virus NP; Influenza A Virus M1; and Influenza B Virus HA and NA. In still further preferred embodiments, immunogenic proteins may include Influenza A Virus HA subtypes H1 and H3; Influenza A Virus NA subtypes N1 and N2; and Influenza A Virus NP, M1, NS1, PA, and PB1; Influenza A Virus HA subtypes H5 and H7, and H9; Influenza A Virus NA subtypes N1, N2, N7, and N9; and Influenza Virus A NP and M1.

Certain preferred embodiments of the invention may include an immunogenic composition in which the polyanhydride nanoparticle comprises by weight about 2.5% HA, about 2.5% NP, and about 2% CpG polynucleotide. Other preferred embodiments of the invention include also polyanhydride nanoparticle comprising by weight about 1% HA, about 1% NP, and about 2% CpG polynucleotide or about 1% HA, about 1% NP, and about 2% R848.

In certain embodiments, the adjuvant may include a Toll-Like Receptor (TLR) agonist, a liposome, a mineral salt, an oil emulsion, a polymer, a polysaccharide, a saponin, R848, or a STING activating adjuvant. Embodiments also may include a second adjuvant in the excipient that may be the same or different than the adjuvant entrapped within a nanoparticle.

Certain preferred embodiments of the invention include a targeting protein disposed on at least a portion of a surface of a nanoparticle that may direct the nanoparticle to a specific cell type. For example, the targeting protein may be an antibody or ligand that specifically binds to CLEC9a, Dectin-1, SIRpa, or MERtK.

Embodiments of the immunogenic composition disclosed herein may be administered to a subject through various delivery routes. Preferably, an immunogenic composition may be delivered intranasally, intramuscularly, subcutaneously, or a combination thereof.

Embodiments of the invention provide several advantageous over the prior art. Most notably, embodiments of the invention allow a user to design an immunogenic composition that may utilize or a take advantage of tissue-specific factors and critical pathways for induction of tissue-specific T and B cell immunogenic response to generate local and systemic immunity.

Advantageously, embodiments of the invention may provide a universal protection against multiple homologous and heterologous strains of influenza virus without any toxicity related to natural influenza virus infections.

Advantageously, embodiments of the invention may be administered intranasal to facilitate immunity in both the upper and lower airway including the formation of local resident T and B memory cells.

Advantageously, the bioerodible or biodegradable properties of the nanoparticles allow for a sustained release of an entrapped immunogen and adjuvant to act as a long-term immunogen depot.

Advantageously, certain embodiments of the invention may induce full adaptive immunity (antigen-reactive B cells, antibody (Ab), CD4 T cells, CD8 T cells) and protection against influenza challenge (both homologous and heterologous) after intranasal (i.n.) administration of immunogenic composition in both the presence and absence of a free antigen component in the excipient.

The present invention and its attributes and advantages will be further understood and appreciated with reference to the detailed description below of presently contemplated embodiments, taken in conjunction with the accompanying drawings.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION OF THE INVENTION

Figure 1:
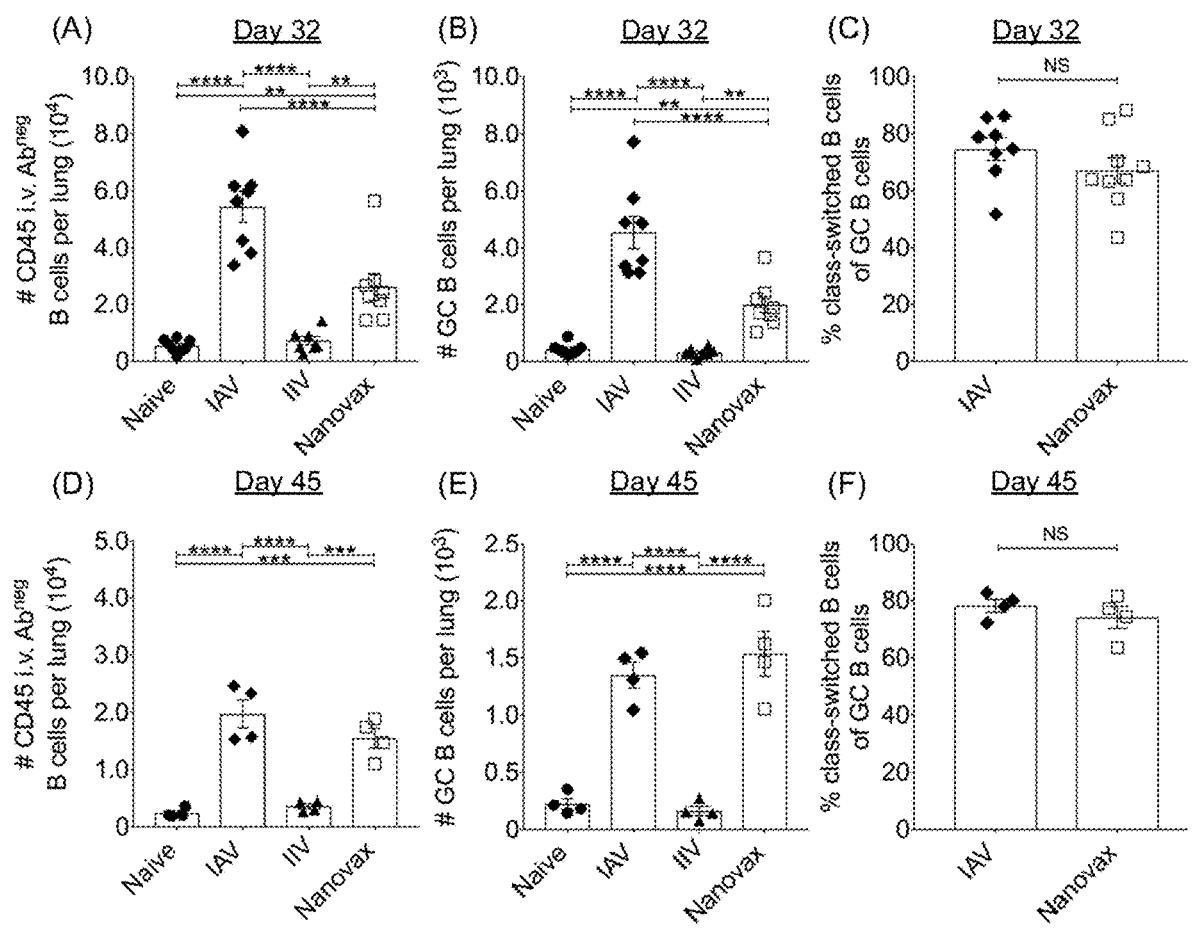
FIG. 1 illustrates vaccination with IAV-nanovax induces lung-resident germinal center B cell responses. C57BL/6 mice were challenged i.n. with a 110 tissue culture infections unit (TCIU) of A/Puerto Rico/8/1934, vaccinated i.m. with IIV, prime+boost vaccinated i.n. with IAV-nanovax (Nanovax) or left unchallenged/unvaccinated (naïve). At 32 and 45 days post challenge/vaccination, (A, D) lung-resident B cells, (B, E) germinal center (GC) B cells, and (C, F) class switched B cells were enumerated within the lungs. Error bars mean±s.e.m. Data are from two pooled experiments (A, B, C; n=8 mice/group) or one (D, E, F; n=4 mice/group) independent experiment. P<0.01, *P<0.001, ****P<0.0001 (One-way ANOVA with Tukey's multiple comparisons test).

The present invention generally is directed to certain immunogenic composition, such as a vaccine, that may include one or more biodegradable polymer nanoparticles containing an effective amount of at least one Influenza Virus immunogenic protein and an adjuvant contained within the interior of the nanoparticle to elicit an immune response and the formation of local tissue resident T and B memory cells.

Preferred embodiments of the invention comprise nanoparticles based on polyanhydride homopolymers and/or copolymers of 1,ω-bis(p-carboxyphenoxy)alkanes and 1,ω- dicarboxylic alkanes such as 1,6-bis(p-carboxyphenoxy) hexane. Other polyanhydride copolymers preferably include poly(bis-(1,ω-carboxyphenoxy)($C_2$-$C_{12}$)alkane-co-($C_5$-$C_{20}$) bis-alkanoic acids). The substituents on the phenoxy moiety may be orientated ortho, meta, or para to each other, and are typically in a para relationship. The alkane moiety of the bis-(carboxyphenoxy) alkane may be a ($C_2$-$C_{12}$)alkane. In more specific embodiments, the alkane moiety may be a ($C_4$-$C_8$)alkane, and more specifically a ($C_6$)alkane. The alkanoic diacids used for the biodegradable polymers may be a ($C_5$-$C_{20}$)alkane bis-carboxylic acid. Specifically, the bis-carboxylic acid may be a ($C_6$-$C_{16}$)alkane bis-carboxylic acid, a ($C_8$-$C_{12}$)alkane bis-carboxylic acid, or more specifically a ($C_{10}$)alkane bis-carboxylic acid. Optionally, the alkane and aryl moieties of the polyanhydride copolymers may be substituted in a manner that increases or decreases hydrophobicity of the nanoparticles. The polymers typically may have the general formula:

$$\left[ \begin{array}{c} O \\ \| \\ O \end{array} \bigcirc \!\!-\!\! O \!\!-\!\! (\,)_a \!\!-\!\! O \!\!-\!\! \bigcirc \!\!-\!\! \begin{array}{c} O \\ \| \\ O \end{array} \right]_m \left[ \begin{array}{c} O \\ \| \\ O \end{array} \!\!-\!\! (\,)_b \!\!-\!\! \begin{array}{c} O \\ \| \\ O \end{array} \right]_n$$

where m and n represent the number of repeating units of each monomer, for example, such that the polymers have molecular weights of about 4,000 to about 55,000. The variables "m" and "n" are not less than one and are typically greater than ten. Alternatively, the polyanhydride homopolymers may also be used, in which case either m or n would be zero. The variable "a" may be about 2-12 and the variable "b" may be about 2-20.

The polyanhydride copolymers may be synthesized, for example, through melt polycondensation from acetylated prepolymers using, for example, the technique described by Kipper et al. ((2002) *Design of an injectable system based on bioerodible polyanhydride microspheres for sustained drug delivery, Biomaterials* 23, 4405-4412)), and U.S. Pat. No. 8,449,916 to Narasimhan et al. The polyanhydrides copolymers also may be prepared by microwave polymerization as described by Vogel et al. ((2004) *Rapid synthesis of polyanhydrides by microwave polymerization, Macromol. Rapid Comm.,* 25, 330-333). Other techniques known to those of skill in the art also may be used to prepare the copolymers. The prepared polyanhydride copolymers can have molecular weights of about 4,000 to about 55,000, specifically about 8,000 to about 30,000, and more specifically about 12,000 to about 22,000.

Any suitable and effective ratio of monomers may be used in the synthesis of the polyanhydride copolymers. For example, the carboxyphenoxyalkane (CPA) to alkanoic diacid (AD) ratio may be about 1:1 to about 1:10. Certain embodiments include monomer ratios of about 1:1, about 1:1.5, about 1:2, about 1:3, about 1:4, about 1:5, and about 1:9.

Preferably, the polyanhydride nanoparticles may degrade through surface-erosion due to the in vivo hydrolysis of anhydride linkages at the surface of the nanoparticle that may result in the controlled release of immunogen(s) to a subject. Surface-erodible biomaterials useful for the delivery of immunogens by the techniques disclosed herein are described by, for example, Narasimhan and Kipper, *Surface-erodible biomaterials for drug delivery* ((2004) *Adv. Chem. Eng.,* 29, 169-218). Microstructural characterization of polyanhydride blends for controlled drug delivery are described by, for example, Mallapragada et al., *Biomaterials for Drug Delivery and Tissue Engineering,* Eds. ((2001) *Mater. Res. Soc. Symp. Proc.* 662, NN4.2.1-4.2.5). Typically, nanoparticles of the invention the nanoparticles are substantially spherical with an average diameter of about 150 nm to about 1 μm and a Polydispersity Index of about 0.1 to about 0.2.

Biodegradable or bioerodible polymers may be used to entrap one or more immunogenic proteins or antigen, and, optionally, one or more adjuvants for delivery to a subject. As used herein, the term "immunogenic protein" refers to a molecule with one or more epitopes that stimulate a host's immune system to make a secretory, humoral and/or cellular antigen-specific response against one or more strains of influenza virus in a vertebrate. The term is also used interchangeably with "immunogen". By way of example, embodiments may include one or more specific immunogenic proteins that may be a complete protein, portions of a protein, a peptide, fusion proteins, glycosylated proteins, and combinations thereof. In certain preferred embodiments, the immunogenic protein is a full-length influenza virus protein.

As used herein, "entrapped" refers to the incorporation or partial incorporation of an immunogenic protein into and/or onto the matrix of a polyanhydride microparticle. The properties of the polymers may be tailored through the selection of various monomers having the appropriate properties for encapsulation/entrapment and delivery of the immunogenic payload, such as, for example, a vaccine. The phase behavior of biodegradable polyanhydride blends is discussed by Kipper et al. ((2004) *Understanding the phase behavior of biodegradable polyanhydride blends using scattering, microscopy, and molecular simulations, Polymer,* 45(10), 3329-3340) and microphase separation in bioerodible polyanhydrides for drug delivery is described by Shen et al. ((2001) *Microphase separation in bioerodible copolymers for drug delivery, Biomaterials,* 22, 201-210) and Kipper et al. ((2005) *Nanoscale morphology of polyanhydride copolymers, Macromolecules,* 38, 8468-8472) and the crystallinity of the homopolymers and copolymers is described by Kipper et al. ((2005) *Morphology of polyanhydrides: time-resolved SAXS studies of crystallization, J. Polym. Sci. Part B: Polym. Phys.,* 43, 463-477).

Preferred immunogenic proteins for use with the nanoparticles may include immunogenic proteins from one or more serotypes of Influenza Virus such as Influenza A virus, Influenza B virus, Influenza C virus, and/or Influenza D virus. Other nanoparticle embodiments may include a mixture of immunogens from two or more Influenza serotypes (e.g. Influenza A Virus and Influenza B virus).

Certain embodiments of nanoparticle may include immunogens from only a single Influenza serotype (e.g. only Influenza A Virus). Alternatively, nanoparticles may include the immunogenic proteins hemagglutinin (H1, H2, H3, H4, H5, H6 H7, H8, H9, H10, H12, H13, H14, H15, H16, H17, and H18) and neuraminidase (N1, N2, N3, N4, N5, N6, N7, N8, N9, N10, and N11) from certain Influenza A virus subtypes.

Exemplary immunogens from influenza A, influenza B, Influenza C, and influenza D virus include also Hemagglutinin (HA) (subtypes H1-H18, HA Yamagata, HA Victoria, H1N1 strains A/Albany/12/1951, A/Beijing/22808/2009, A/Beijing/262/1995, A/Brevig Mission/1/1918, A/Brisbane/59/2007, A/California/04/2009, A/California/06/2009, A/California/07/2009, A/Chile/1/1983, A/England/195/2009, A/England/42/1972, A/New Caledonia/20/1999, A/New York/06/2009, A/New York/1/1918, A/New York/18/2009, A/New Jersey/8/1976, A/Ohio/07/2009, A/Ohio/UR06-0091/2007, A/Puerto Rico/8/1934, A/Puerto Rico/8/34/Mount Sinai, A/Solomon Islands/3/2006, A/swine/Belgium/1/1998, A/Swine/Wisconsin/136/1997, A/Taiwan/01/1986, A/Texas/05/2009, A/Texas/36/1991, A/USSR/90/1977, A/USSR/92/1977, A/WSN/1933, A/Wilson-Smith/33, A/Tientsin/78/77, A/Singapore/6/86, A/Memphis/39/83, A/Malaysia/54, A/Iowa/43, A/Hong Kong/117/77, A/Fort Monmouth/1/47, A/Baylor/4052/81, A/Albany/4835/48; H1N2 strain A/swine/Guangxi/13/2006, A/Singapore/1/1957; H1N3 strain A/duck/NZL/160/1976; H2N2 Strain A/Ann Arbor/6/1960, A/Canada/720/2005, A/Guiyang/1/1957, A/Japan/305/1957; H3N2 strain A/Aichi/2/1968, A/Babol/36/2005, A/Brisbane/10/2007, A/California/7/2004, A/Chiang Rai/277/2011, A/Christchurch/4/1985, A/Fujian/411/2002, A/Guangdong-Luohu/1256/2009, A/HongKong/1/1968, A/Hong Kong/CUHK31987/2011, A/Indiana/07/2012, A/Memphis/1/68, A/Moscow/10/1999, A/New York/55/2004, A/Perth/16/2009, A/reassortant/IVR-155, A/Sydney/5/1997, A/Texas/50/2012, A/Victoria/208/2009, A/Victoria/210/2009, A/Victoria/3/1975, A/Victoria/361/2011, A/Wisconsin/15/2009, A/Wisconsin/67/X-161/2005, A/Wyoming/03/2003, A/X-31; H3N8 strains A/canine/New York/145353/2008, A/equine/Gansu/7/2008; H4N2 strain A/duck/Hunan/8-19/2009; H4N4 A/mallardduck/Alberta/299/1977, H4N6 A/mallard/Ohio/657/2002, A/Swine/Ontario/01911-1/99; H4N8 A/chicken/Alabama/1/1975; H5N1 strain, A/HongKong/156/97, A/chicken/Shanxi/2/06, A/silky chicken/Hong Kong/SF189/01, A/chicken/Henan/16/04 (H5N1), A/Anhui/1/2005, A/barheadedgoose/Qinghai/14/2008, A/bar-headedgoose/Qinghai/1A/2005, A/barnswallow/Hong Kong/D10-1161/2010, A/Cambodia/R0405050/2007, A/Cambodia/S1211394/2008, A/chicken/Egypt/2253-1/2006, A/chicken/India/NIV33487/2006, A/chicken/Jilin/9/2004, A/chicken/VietNam/NCVD-016/2008, A/chicken/Yamaguchi/7/2004, A/Common magpie/HongKong/2256/2006, A/commonmagpie/Hong Kong/5052/2007, A/Duck/HongKong/p46/97, A/duck/Hunan/795/2002, A/duck/Laos/3295/2006, A/Egypt/2321-NAMRU3/2007, A/Egypt/3300-NAM RU3/2008, A/Egypt/N05056/2009, A/goose/Guangdong/1/96, A/goose/Guiyang/337/2006, A/Hongkong/213/03, A/HongKong/483/97, A/Hubei/1/2010, A/Hubei/2011, A/hubei/2011-CDC, A/Indonesia/5/2005, A/Japanesewhite-eye/HongKong/1038/2006, A/Thailand/1(KAN-1)/2004, A/turkey/Turkey/1/2005, A/Vietnam/UT31413II/2008, A/whooper swan/Mongolia/244/2005, A/Xinjiang/1/2006; H5N2 strain A/American green-winged teal/California/HKWF609/07, A/ostrich/South Africa/AI1091/2006; H5N3 strain A/duck/Hokkaido/167/2007; H5N8 strain A/breeder duck/Korea/Gochang1/2014, A/broilerduck/Korea/Buan2/2014, A/duck/Jiangsu/k1203/2010, A/duck/NY/191255-59/2002, A/duck/Zhejiang/6D18/2013, A/duck/Zhejiang/W24/2013, A/turkey/Ireland/1378/1983; H5N9 strain A/chicken/Italy/22A/1998; H6N1 strain A/northern shoveler/California/HKWF115/2007; H6 N4 strain A/chickenHongKong/17/77; H6N5 strain A/shearwater/Australia/1/1973; H6N6 strain A/duck/Eastern China/11/2009; H6N8 strain A/mallard/Ohio/217/1998; H7N1 strain A/turkey/Italy/4602/99; H7N2 strain A/ruddy turnstone/New Jersey/563/2006, H7N3 strain A/chicken/SK/H R-00011/2007, A/turkey/Italy/214845/2002; H7N7 strain A/chicken/Netherlands/1/03, A/equine/Kentucky/1a/1975, A/Netherlands/219/2003; H7N8 strain A/mallard/Netherlands/33/2006; H7N9 strain A/Anhui/1/2013, A/Anhui/PA-1/2013, A/chicken/Zhejiang/DTID-ZJU01/2013, A/Hangzhou/1/2013, A/Hangzhou/3/2013, A/Huzhou/10/2013, A/Pigeon/Shanghai/S1069/2013, A/Shanghai/1/2013, A/Shanghai/4664T/2013, A/Shanghai/Patient3/2013, A/Zhejiang/1/2013, A/Zhejiang/DTID-ZJU10/2013; H8N4 strain A/pintail duck/Alberta/114/1979; H9N2 strain A/brambling/Beijing/16/2012, A/Chicken/Hong Kong/G9/1997, A/duck/Hong Kong/448/78, A/Guinea fowl/Hong Kong/WF10/99, A/Hong Kong/1073/99, A/Hong Kong/2108/2003, A/Hong Kong/3239/2008, A/Hong Kong/35820/2009; H9N5 strain A/shorebird/DE/261/2003; H9N8 strain A/chicken/Korea/164/04; H10N3 strain A/duck/Hong Kong/786/1979, A/duck/Hunan/S11205/2012, A/mallard/Minnesota/Sg-00194/2007; H10N4 strain A/mink/Sweden/3900/1984; H10N7 strain A/blue-winged teal/Louisiana/Sg-00073/2007; H10N8 strain A/duck/Guangdong/E1/2012, A/Jiangxi-Donghu/346/2013; H10N9 strain A/duck/Hong-Kong/562/1979, A/duck/Hong Kong/562/1979; H11N2 strain A/duck/Yangzhou/906/2002, A/thick-billed murre/Newfoundland/031/2007; H11N6 strain A/duck/England/1/1956; H11N9 strain A/mallard/Alberta/294/1977; H12N1 strain A/mallard duck/Alberta/342/1983; H12N3 strain A/bar headed goose/Mongolia/143/2005; H12N5 strain A/green-winged teal/ALB/199/1991; H13N6 strain A/black-headed gull/Sweden/1/1999; H13N8 A/black-headed gull/Netherlands/1/00; H14N5 strain A/Mallard/Astrakhan(Gurjev)/263/1982; H15N2 strain A/Australian shelduck/Western Australia/1756/1983; H15N2 strain A/duck/AUS/341/1983; H16N3 strain A/black-headed gull/Sweden/5/99; H17N10 strain A/little yellow-shouldered bat/Guatemala/164/2009; H18N11 strain A/flat-faced bat/Peru/033/2010), Influenza B Virus strain B/Brisbane/3/2007, B/Brisbane/60/2008, B/Florida/07/2004, B/Florida/4/2006, B/Hong Kong/05/1972, B/Malaysia/2506/2004, B/Massachusetts/03/2010, B/Ohio/01/2005, B/PHUKET/3073/2013, B/Utah/02/2012, B/Victoria/02/1987, B/Victoria/504/2000, B/Wisconsin/01/2012, B/Yamagata/16/1988; Neuraminidase (NA) (subtypes N1-N11, NA Yamagata, NA Victoria), Nucleocapsid Protein (NP), Matrix Protein 1 (M1), Matrix Protein 2 (M2), Polymerase Basic Protein 1 (PB1), Polymerase Basic Protein 2 (PB2), Polymerase Acidic Protein (PA), Nonstructural Proteins 1 (NS1), Nonstructural Proteins 2/Nuclear Export Protein (NS2/NEP), Polymerase Basic Protein 1 Segment Second Proteins (PB1-F2), Influenza B Virus Membrane Protein (BM2), Influenza B Virus Membrane Protein (NB), Influenza A Virus Segment 2 Alternative Splicing Protein (M42), Influenza A Virus Segment 1 Alternative Splicing Protein (PB2-S1), Influenza A Virus Segment 2 Alternative Initiation Protein (N40)), Influenza A Virus Segment 3Ribosomal Shift Protein (PA-X), Influenza A Virus Segment 3 Alternative Initiation Protein (PA-N182), Influenza A Virus Segment 3 Alternative Initiation Protein (PA-N155), Influenza C/D Virus Polymerase Complex Protein (P3), Influenza C/D Virus Surface Glycoproteins: Hemagglutinin, Esterase, and Fusion activities (HEF), Influenza C/D Virus Matrix Protein (CM1), or Influenza C/D Virus surface glycoprotein CM2.

In preferred embodiments of the invention, influenza A immunogenic proteins include HA (subtypes H1, H2, H3, H4, H5, H6, H7, H8, H9, H10, H11, H12, H13, H14, H15, H16, H17, H18), NA (subtypes N1, N2, N3, N4, N5, N6, N7, N8, N9, N10, N11), NP, M1, M2, PB1, PB2, NS1, NS2/NEP, PA, PB1-F2, M42, PB2-S1, N40, PA-X, PA-N182, and PA-N155; influenza B immunogens include HA Yamagata, HA Victoria, NA Yamagata, NA Victoria, NP, M1, M2, PB1, PB2, NS1, NS2/NEP, PA, and NB; influenza C immunogens include HEF, NP, M1, M2, PB1, PB2, NS1, NS2/NEP, and P3; influenza D immunogens include HEF, NP, M1, M2, PB1, PB2, NS1, NS2/NEP, and P3.

Nanoparticles of the present inventions may include any combination of immunogenic proteins disclosed above. Preferred nanoparticles embodiments may include the following immunogens: Influenza A Virus HA subtypes H1 and H3, Influenza A Virus NA subtypes N1 and N2, Influenza A Virus NP; Influenza A Virus M1, and Influenza B Virus HA and NA; Influenza A Virus HA subtypes H1 and H3, Influenza A Virus NA subtypes N1 and N2, and Influenza A Virus NP, M1, NS1, PA, and PB1; Influenza A Virus HA subtypes H5 and H7, and H9, Influenza A Virus NA subtypes N1, N2, N7, and N9, and Influenza Virus A NP and M1.

Certain preferred embodiments also include one or more adjuvants. As used herein, the term "adjuvant" refers to a compound that may augment, enhance and/or boost the immune response to an immunogen. However, when the compound is administered alone, it does not generate an immune response to the immunogen. In some embodiments, the adjuvant generates an immune response to the immunogen and does not produce an allergy or other adverse reaction. Adjuvants can enhance an immune response by several mechanisms including, e.g., lymphocyte recruitment, stimulation of B and/or T cells, and stimulation of macrophages.

Specific examples of adjuvants include, but are not limited to, aluminum salts (such as aluminum hydroxide, aluminum phosphate, and aluminum sulfate), 3 De-O-acylated monophosphoryl lipid A (MPL) (see GB 2220211), MF59 (Novartis), AS03 (GlaxoSmithKline), AS04 (GlaxoSmithKline), polysorbate 80 (Tween 80; ICL Americas, Inc.), imidazopyridine compounds (see International Application No. PCT/US2007/064857, published as International Publication No. WO2007/109812), imidazoquinoxaline compounds (see International Application No. PCT/US2007/064858, published as International Publication No. WO 2007/109813) and saponins, such as QS21 (see Kensil et al., in Vaccine Design: The Subunit and Adjuvant Approach (eds. Powell & Newman, Plenum Press, N Y, 1995); and U.S. Pat. No. 5,057,540 to Kensil et al.). In some embodiments, the adjuvant is Freund's adjuvant (complete or incomplete). Other adjuvants include oil in water emulsions (such as squalene or peanut oil), cholera toxin B subunit, flagellin, human papillomavirus L1 or L2 protein, herpes simplex glycoprotein D (gD), complement C4 binding protein, TL4 ligand, and IL-1 beta, lysolecithin, pluronic polyols, polyanions, dinitrophenol, iscomatrix, liposome polycation DNA particles, and CpG polynucleotides. Furthermore, adjuvants and specific examples of adjuvants that can be included in the nanoparticles are provided in the table below.

| Adjuvant Class | Examples |
| --- | --- |
| Liposomes | AS01 |
| | Virosomes |
| | Virus-like particles |
| Mineral Salts | Aluminum hydroxide |
| | Aluminum phosphate |
| | Calcium phosphate |
| Oil Emulsions | MF59 |
| | AS02 |
| | AS03 |
| Polymers | Polyanhydrides (CPH, CPP, SA, CPTEG) |
| | Polysulfones |
| | Polyesters (PLGA, PLA, PCL) |
| | Micelles (PDEAEM, Pluronic F127) |
| | Polyethers (PEG) |

-continued

| Adjuvant Class | Examples |
| --- | --- |
| | Poly(vinyl alcohol) |
| | Chitosan |
| Polysaccharides | β-glucans |
| | Mannose |
| Saponins | Quillaja saponins |
| | Quill A |
| | QS-21 |
| | ISCOMs |
| STING-activating | cyclic dinucleotides (CDNs) |
| | R,R-CDG |
| TLR Agonists | CpG Oligodeoxynucleotide |
| | Poly I:C |
| | Imiquimod/Resiquimod |
| | MPLA |
| | Flagellin |
| | AS04 |

One or more of these adjuvants can be encapsulated within nanoparticles and be suitable for intranasal delivery and others can be blended or cocktailed with the nanoparticles and be suitable for parenteral delivery.

Figure 23:
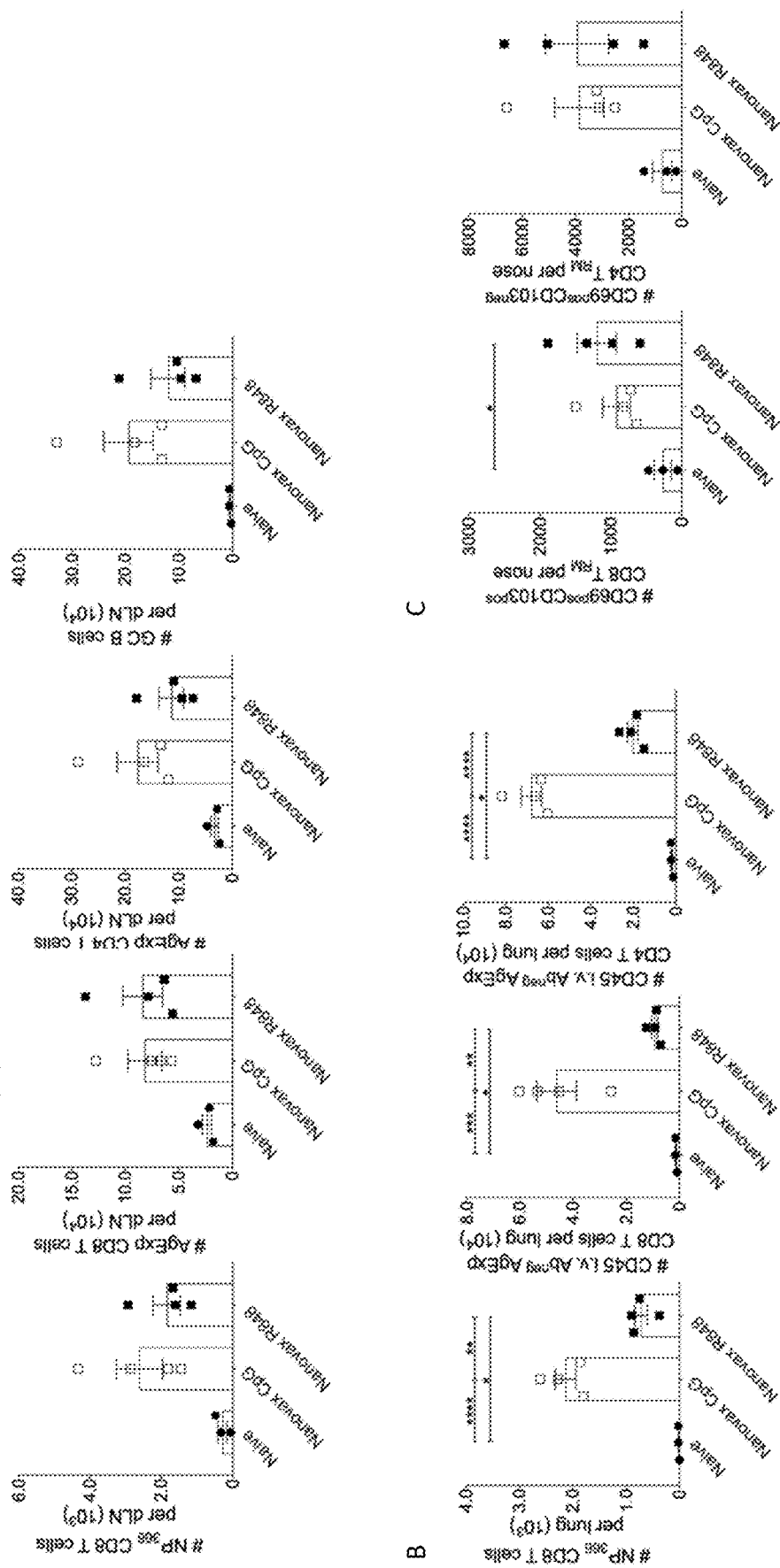
FIG. 23 illustrates that IAV-nanovax R848 induces influenza specific B cell and T cell responses. C57BL/6 mice received a prime+boost i.n. vaccination with either IAV-Nanovax (i.e. Nanovax CpG) or an IAV-nanovax containing R848 (Nanovax R848). At day 25 post vaccination, (A) lung draining lymph nodes, (B) lungs, and (C) nasal tissue was harvested and analyzed. (A) Shown are the number of IAV NP$_{366}$-specific CD8 T cells, AgExp CD8 T cells (CD11a$^{hi}$CD8α$^{lo}$), AgExp CD4 T cells (CD4$^+$CD11a$^{hi}$CD49d$^{pos}$) and germinal center B cells (CD19$^+$B220$^+$PNA$^+$) in the lung draining lymph nodes. (B) Shown are the number of IAV NP$_{366}$-specific CD8 T cells, lung-resident AgExp CD8 T cells (CD11a$^{hi}$CD8α$^{lo}$CD45 i.v.Ab$^{neg}$), and lung-resident AgExp CD4 T cells (CD4$^+$CD11a$^{hi}$CD49d$^{pos}$CD45 i.v.Ab$^{neg}$) in the lungs. (C) Shown are the number of nasal-resident AgExp Trm CD4 T cells (CD4$^+$CD11a$^{hi}$CD49d$^{pos}$CD45 i.v.Ab$^{neg}$CD69$^+$CD103$^-$) and nasal-resident AgExp Trm CD8 T cells (CD11a$^{hi}$CD8α$^{lo}$CD45 i.v.Ab$^{neg}$CD69$^+$CD103$^+$). These results show that an IAV-nanovax formulation containing a different adjuvant still induces IAV-specific T cell and B cell responses.

In preferred embodiments, the adjuvants may include a Toll-Like Receptor ("TLR") agonist. The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, a TLR5 agonist (e.g. flagellin), a TLR7 agonist (e.g. R848, see FIG. 23), and/or aTLR9 agonist (e.g. CpG oligodeoxynucleotide).

It is contemplated that one or more adjuvants may be entrapped in the interior of a polyanhydride nanoparticle. Alternatively, compositions of the invention may include an adjuvant in an excipient, but not in the interior of the nanoparticle. In some embodiments, both the nanoparticle and the excipient may include one or more adjuvants.

One preferred embodiment of the invention includes a biodegradable polyanhydride nanoparticle comprising one or more polyanhydride copolymers forming the nanoparticle, the copolymers include 1,8-bis(p-carboxyphenoxy)-3,6-dioxaoctane (CPTEG) and 1,6-bis(p-carboxyphenoxy) hexane (CPH) in a ratio of about 20:80; one or more immunogenic proteins of an Influenza Virus, the Influenza Virus selected from the group consisting of Influenza A Virus, Influenza B Virus, Influenza C Virus, and Influenza D Virus; and an adjuvant entrapped within an interior of the nanoparticle.

In another preferred embodiment of a nanoparticle, the immunogenic proteins comprise by weight about 1% hemagglutinin, about 1% nucleocapsid protein, and about 2% CpG oligodeoxynucleotide adjuvant.

In some embodiments, the nanoparticles may be at least partially surface coated with a targeting molecule such as a ligand or anti-receptor antibody that may specifically target the nanoparticle to a specific cell type or cell population. For example, a coated nanoparticle may be directed to a specific lung dendritic cell populations or macrophage populations.

The nanoparticles can persist in the lungs for more than two months, gradually releasing encapsulated contents as the nanoparticles bioerode. Specifically, the 20:80 CPTEG: CPH nanoparticles are visible in the lungs for at least 63 days. The hydrophobic chemistry of this formulation (high CPH content), coupled with the thermal properties of the copolymer enable facile synthesis of nanoparticles that have highly effective persistence time in the lungs. The persistence time is highly advantageous because reduced CPH content in the copolymer may result in shorter persistence (lessening the depot effect) and increased CPH content may lead to tolerance and/or difficulty in preparing nanoparticle-based formulations suitable for intranasal delivery. The 20:80 CPTEG:CPH formulation therefore provides a balance of advantageous persistence kinetics as well as facile synthesis suitable for intranasal delivery.

In certain preferred embodiments, the targeting protein may be an antibody or ligand that specifically binds to the surface proteins or receptors on target cells including C-type Lectin Domain family 9 member A (CLEC9a), C-type Lectin Domain family 7 member A (Dectin-1), Signal Regulatory Protein-1 (SIRP1), or MER Receptor Tyrosine Kinase (MERtK).

The immunogen-loaded nanoparticles may be prepared by the water/oil/oil double emulsion technique similar to the method reported by Esparza and Kissel for poly(D,L-lactide-co-glycolide) microspheres (Esparza et al., (1992) *Parameters affecting the immunogenicity of microencapsulated tetanus toxoid, Vaccine* 10, 714-720). The polymer is dissolved in an organic solvent such as methylene chloride (typically about 20-30 mg/mL). Any suitable solvent can be used to dissolve the polymer. Suitable examples include chlorinated organic solvents such as methylene chloride, chloroform, and carbon tetrachloride. The immunogen is dissolved in pure water (typically about 0.5-2 mg dialyzed and lyophilized immunogen per 25 μL of water). The immunogen solution is added to the polymer solution in a centrifuge tube and immediately emulsified by agitation with a handheld homogenizer. While still homogenizing, silicone oil saturated with methylene chloride is added drop wise to form the microparticles and the mixture is further homogenized.

The loaded nanoparticles may be precipitated by transferring the double emulsion to a container of cold n-heptane (non-solvent). The mixture may then be rapidly stirred with an impeller to extract the solvent. Non-solvent may be periodically added to replace volume lost due to evaporation. The nanoparticles may then be isolated by filtration. The microparticles may then be rinsed with additional non-solvent and dried under vacuum to afford a free-flowing powder.

Nanoparticles also may be prepared by modifications of the solvent removal technique described above. Suitable modifications may include, but are not limited to a water/oil/water emulsion, a solid/oil/water/emulsion, or spray drying techniques well known to those skilled in the art.

The nanoparticles, immunogens, and adjuvants described herein may be used to prepare therapeutic pharmaceutical compositions, for example, by combining the nanoparticles and adjuvants with a pharmaceutically acceptable diluent, excipient, or carrier. The nanoparticles may be added to a carrier in the form of a salt or solvate. For example, in cases where nanoparticles are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and γ-glycerophosphate. Suitable inorganic salts also may be formed, including hydrochloride, halide, sulfate, nitrate, bicarbonate, and carbonate salts, sodium chloride, calcium chloride, sodium phosphate, monosodium glutamate, and aluminum salts (e.g., aluminum hydroxide, aluminum phosphate, alum (potassium aluminum sulfate), or a mixture of such aluminum salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The immunogenic composition may include preservatives such as thiomersal or 2-phenoxyethanol. It is preferred, however, that the vaccine should be substantially free from (i.e. less than 5 g/ml) mercurial material e.g. thiomersal-free. Immunogenic compositions containing no mercury are more preferred. Preservative-free immunogenic compositions are particularly preferred.

To control tonicity, it is preferred to include a physiological salt, such as a sodium salt. Sodium chloride (NaCl) is preferred, which may be present at between 1 and 20 mg/ml, e.g., about 10±2 mg/ml NaCl. Other salts that may be present include potassium chloride, potassium dihydrogen phosphate, disodium phosphate dehydrate, magnesium chloride, calcium chloride, etc.

Immunogenic compositions further may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8. The composition is preferably sterile. The composition is preferably non-pyrogenic e.g. containing <1 EU (endotoxin unit, a standard measure) per dose, and preferably <0.1 EU per dose. The composition is preferably gluten free.

In certain embodiments, the immunogenic composition includes as an excipient such as water or phosphate buffered saline.

Immunogenic compositions (such as a vaccine) may be formulated and administered in accordance with standard techniques well known to those skilled in the art. For example, a vaccine can be prepared by any suitable method, such as the methods described by Franchini et al., (International Patent Publication PCT/US2003/035499), Kipper et al., (U.S. Pat. No. 7,858,093), or Caputa et al. (U.S. Pat. No. 5,554,371, for example, at col. 7). Other useful techniques can be used such as those described by Cleary (U.S. Pat. No. 5,846,547, for example, at col. 6-7). One preferred immunogenic composition may comprise one or more polyanhydride copolymers forming a biodegradable first polyanhydride nanoparticle, the copolymers including 1,8-bis(p-carboxyphenoxy)-3,6-dioxaoctane (CPTEG) and 1,6-bis(p-carboxyphenoxy)hexane (CPH) in a ratio of about 20:80, one or more immunogenic proteins of an Influenza Virus and an adjuvant within an interior of the nanoparticle, and an excipient. The immunogenic compositions may include nanoparticles that comprise a mixture of various immunogens, such as those listed above. Alternatively, immunogenic compositions may include a mixture of nanoparticles, where each of the nanoparticles includes a single immunogen.

Embodiments of immunogenic compositions also may include one more free immunogenic proteins in the excipient that may be the same or different than the immunogenic proteins entrapped within the nanoparticles in the composition. For example, an immunogenic composition may include free hemagglutinin and neuraminidase proteins in the excipient. Further, certain embodiments of an immunogenic compositions of the present invention may include one or more adjuvants in the excipient. The free adjuvant may be the same or different than the adjuvant, if any, entrapped within a nanoparticle.

Immunogenic compositions or nanoparticles may be administered to a subject by a variety of routes. These include, but are not limited to, intranasal, intratracheal, oral, intradermal, intramuscular, intraperitoneal, transdermal, intravenous, conjunctival, and subcutaneous routes. In some embodiments, a composition is formulated for topical administration, for example, for application to the skin. In a preferred embodiment, the route of administration is nasal, e.g., as part of a nasal spray. In certain embodiments, an immunogenic composition is formulated for intramuscular administration. In some embodiments, an immunogenic composition is formulated for subcutaneous administration.

It is further contemplated that an immunogenic composition of the invention may be administered through a combination of administration routes, or one or more administrations of composition using the same route of delivery. For example, an intranasal dosing may be delivered to the subject prior to an intramuscular dosing or subcutaneous administration. Alternatively, an intranasal dosing may be delivered to the subject subsequent to intramuscular dosing or subcutaneous administration.

For administration to a subject, a first immunogenic composition may be administered to the individual (prime) and then after a period of time, a second immunogenic composition may be administered to the individual (boost). Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks. In one embodiment, the boosting composition is formulated for administration about 1 week, or 2 weeks, or 3 weeks, or 4 weeks, or 5 weeks, or 6 weeks, or 7 weeks, or 8 weeks, or 9 weeks, or 16 weeks, or 20 weeks, or 24 weeks, or 28 weeks, or 32 weeks after administration of the priming composition. Priming and boosting may be accomplished through one or more of the means disclosed herein (e.g. a nasal prime and nasal boost etc.). The means of administration of the prime and boost need not be the same (e.g. a nasal prime and intramuscular boost etc.).

The first and second immunogenic compositions may be, but need not be, the same composition. Thus, in one embodiment of the present invention, the step of administering the immunogenic composition to a subject comprises administering a first immunogenic composition, and then at a later time, administering a second immunogenic composition.

It is contemplated that any embodiment discussed in this specification may be implemented with respect to any method, kit, reagent, or composition, and vice versa. Furthermore, the compositions may be used to achieve methods of the invention.

Embodiments of the immunogenic composition of the invention also may include material for a single administration or may include material for multiple administrations (i.e., a 'multidose' kit). The inclusion of a preservative is preferred in multidose arrangements. As an alternative (or in addition) to including a preservative in multidose compositions, the compositions may be stored in a container having an aseptic adaptor for removal of material.

Definitions

Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: A Comprehensive Desk Reference, published by Wiley, John & Sons, Inc., 1995 (ISBN 0471186341).

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

An "effective amount" refers to an amount effective to kill a cell, inhibit a cell from growing or dividing, treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping, or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

As used herein, "pharmaceutically acceptable" carrier or excipient includes any and all solvents, dispersion media, coatings, antibacterial and antifungal agents, isotonic and absorption/resorption delaying agents, and the like that are physiologically compatible. Preferably, the carrier is suitable for injection or infusion. Pharmaceutically acceptable carriers include sterile aqueous solutions or dispersions and sterile powders for the preparation of sterile injectable solutions or dispersion. The use of such media and agents for pharmaceutically active substances is known in the art. In addition to water, the carrier can be, for example, an isotonic buffered saline solution.

As used herein, the terms "purified" and "isolated" when used in the context of a polypeptide (including an antibody) that is obtained from a natural source, e.g., cells, refers to a polypeptide which is substantially free of contaminating materials from the natural source, e.g., soil particles, minerals, chemicals from the environment, and/or cellular materials from the natural source, such as but not limited to cell debris, cell wall materials, membranes, organelles, the bulk of the nucleic acids, carbohydrates, proteins, and/or lipids present in cells. Thus, a polypeptide that is isolated includes preparations of a polypeptide having less than about 30%, 20%, 10%), 5%, 2%, or 1%> (by dry weight) of cellular materials and/or contaminating materials. As used herein, the terms "purified" and "isolated" when used in the context of a polypeptide (including an antibody) that is chemically synthesized refers to a polypeptide which is substantially free of chemical precursors or other chemicals which are involved in the syntheses of the polypeptide.

As used herein, terms "subject" or "patient" are used interchangeably to refer to an animal (e.g., birds, reptiles, and mammals). In a specific embodiment, a subject is a bird. In another embodiment, a subject is a mammal including a non-primate (e.g., a camel, donkey, zebra, cow, pig, horse, goat, sheep, cat, dog, rat, and mouse) and a primate (e.g. a monkey, chimpanzee, and a human). In certain embodiments, a subject is a non-human animal. In another embodiment, a subject is a human.

The following examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Polyanhydride Nanovaccine Induces Robust Pulmonary B and T Cell Immunity and Confers Protection Against Homologous and Heterologous Influenza A Virus Infections Influenza A virus (IAV) is a major cause of worldwide respiratory illness. Given the disease severity, associated economic costs, and recent appearance of novel IAV strains, there has been a renewed interest in developing novel and efficacious "universal" IAV vaccination strategies. It is thought that immunizations capable of generating local (i.e., nasal mucosa and lung) tissue-resident memory T and B memory cells in addition to systemic immunity offer the greatest protection against future IAV encounters. Current IAV vaccines are designed to largely stimulate IAV-specific antibodies, but do not generate the lung-resident memory T and B cells induced during IAV infections. Disclosed herein is intranasally administered biocompatible polyanhydride nanoparticle-based IAV vaccine (IAV-nanovax) capable of providing robust protection against subsequent homologous and heterologous IAV infections. Our findings also demonstrate that vaccination with IAV-nanovax is associated with the induction of germinal center B cells within the lungs, both systemic and lung local IAV-specific antibodies, and IAV-specific lung-resident memory CD4 and CD8 T cells. Altogether the findings show that an intranasally administered nanovaccine may induce immunity within the lungs, similar to what occurs during IAV infections, and thus may be useful as a strategy for providing "universal" protection against IAV.

Materials and Methods

IAV-Nanovax Synthesis.

Monomers based on 1,8-bis(p-carboxyphenoxy)-3,6-dioxoctane (CPTEG) and 1,6-bis(p-carboxyphenoxy)hexane (CPH) were synthesized as described in Torres et al., *Synthesis and characterization of novel polyanhydrides with tailored erosion mechanisms*. Journal of biomedical materials research Part A (2006) 76(1):102-10. Epub 2005/09/03. doi: 10.1002/jbm.a.30510. Using these monomers, 20:80 CPTEG:CPH copolymer was synthesized using melt polycondensation for approximately six hours. The final copolymer composition, purity, and molecular weight of the copolymer were characterized using $^1$H HNMR (DXR 500, Bruker, Billerica, Mass.). Next, 20:80 CPTEG:CPH nanoparticles containing 1% H1 HA, 1% NP, and 2% CpG1668 were synthesized via solid-oil-oil double emulsion (Ulery et al., *Polymer chemistry influences monocytic uptake of polyanhydride nanospheres*. Pharmaceutical Research (2009) 26(3):683-90. Epub 2008/11/07. doi: 10.1007/s11095-008-9760-7.). Briefly, HA and NP protein antigens (Sino Biological, Beijing, China) were dialyzed to nanopure water and lyophilized overnight. The 20:80 CPTEG:CPH copolymer, along with HA, NP, and CpG (ODN 1668, Invivogen, San Diego, Calif.), was dissolved at a polymer concentration of 20 mg/mL in methylene chloride. The solution was sonicated for 30 s and then precipitated into chilled pentane (at a methylene chloride:pentane ration of 1:250). The resulting nanoparticles were collected via vacuum filtration and scanning electron microscopy (FEI Quanta 250, FEI, Hillsboro, Oreg.) was used to characterized morphology and size.

Mice, Vaccination, and Influenza Virus Infection.

Wild type female C57BL/6 mice were bred, housed, and maintained in the University of Iowa (Iowa City, Iowa) animal care facilities. Swiss-Webster mice (NCI Cr:SwWEB) were purchased from Charles River Laboratories, Inc (Frederick, Md.) and maintained in the University of Iowa (Iowa City, Iowa) animal care facilities. All procedures were performed on matched mice, were approved by the Institutional Animal Care and Use Committee of the University of Iowa and comply with the NIH Guide for Care and Use of Laboratory Animals. Mice were randomly assigned into groups for each experiment.

Prior to i.n. IAV-nanovax vaccinations and IAV infections, mice were anesthetized with isoflurane. For each IAV-nanovax i.n. administration, mice received 500 µg of IAV-nanovax (containing a total of 5 µg HA+5 µg NP+10 µg CpG1668) in 50 µL of PBS containing 2.5 µg each of free HA and NP proteins. In prime+boost experiments, mice received a second i.n. dose of IAV-nanovax 14 days after the initial IAV-nanovax priming. For those experiments utilizing IAV-nanovax vaccination without the free antigen component, mice received i.n. 500 µg of IAV-nanovax (containing a total of 5 µg HA+5 NP+10 µg CpG1668) in 50 µL of PBS followed by a second i.n. dose of IAV-nanovax without free antigen 14 days after the initial IAV-nanovax priming. For those experiments utilizing vaccination with polyanhydride particles that only contained CpG1668 (CpG Particles), mice received i.n. 500 µg of CpG Particles in 50 µL of PBS. For IAV infections, mice were infected i.n. with a 110 TCIU or 1108 TCIU dose of mouse adapted A/Puerto Rico/8/34 (H1N1) or a 390 TCIU dose of A/Hong Kong/1/68 (H3N2) strains in 50 µL Iscove's Modified Dulbecco's Medium. After infection mice were euthanized upon reaching 70% of their starting weight. For IIV vaccinations, non-anesthetized mice received either one dose or two doses separated by 14 days of 20 µg of beta-propiolactone inactivated A/Puerto Rico/8/34 (H1N1) IAV in 200 µL of PBS i.m. in the caudal thigh muscle.

For vaccinations utilizing 2x Nanovax, mice received one dose of 500 µg of 2× Nanovax (2.5% HA, 2.5% NP, and 2% CpG1668) i.n. in 50 µL of PBS. For vaccinations utilizing Nanovax-Qdot particles, mice received one dose of 500 µg of Nanovax Qdot (1% HA, 1% NP, 5% Qdot650, 2% CpG1668) i.n. in 50 µL of PBS. For PR8-LAIV vaccinations, mice were vaccinated as described in Waring et al., *MicroRNA-Based Attenuation of Influenza Virus across Susceptible Hosts*. J Virol, 2018. 92(2). Briefly, non-anesthetized mice received 5 µL per nostril of stock live-attenuated cold-adapted influenza A virus that is composed of the six internal genes of A/Ann Arbor/6/60 H2N2 virus and the two external genes of A/Puerto Rico/8/34 H1N1 virus. For s.c. IAV-nanovax vaccinations, the left and right rear footpad of each mouse received 250 ug of IAV-nanovax in 25 uL of PBS (500 ug IAV-nanovax total per mouse).

Measurement of Airway Resistance.

Enhanced pause (Penh), an indicator of lung function (i.e., airway resistance), was measured using unrestrained whole-body plethysmography (Buxco Electronics, Wilmington, N.C.) on non-anesthetized mice. Penh values were recorded daily based on volume and pressure changes over five minutes.

Measurement of Influenza Virus Titers.

Lung viral titers were analyzed by plaque assay on whole lung homogenates. Briefly, serial dilutions of homogenized lung samples were applied to confluent Madin-Darby canine kidney epithelial cell layers and incubated for one hour at 37° C. Cell layers were washed and a minimum essential media agar overlay was applied and incubated for three days at 37° C. Cell layers were fixed in 4% formaldehyde, blocked with 5% milk, and plaques were detected with polyclonal anti-IAV A/Puerto Rico/8/34 (H1N1) chicken antiserum (NR-3098; BEI Resources), peroxidase-conjugated AffiniPure rabbit anti-chicken IgY (Jackson Immunoresearch, West Grove, Pa.), and TrueBlue® peroxidase substrate (KPL, Gaithersburg, Md.).

Intravascular Stain to Determine Cellular Localization.

Three minutes prior to euthanasia, mice were administered 1 µg of fluorophore-conjugated rat anti-mouse CD45.2 (clone 104; BioLegend, San Diego, Calif.) in 200 µL of PBS by retroorbital intravenous injection as previously described.

Tissue and Cell Preparation.

Prior to euthanasia, blood was collected in heparinized capillary tubes (Fisher Scientific, Pittsburgh, Pa.) for subsequent single-cell analysis by flow cytometry and non-heparinized capillary tubes (Fisher Scientific) for serum collection. For cell harvests, these blood samples were then treated with ammonium-chloride-potassium lysis buffer for five minutes at room temperature and washed 1× with flow cytometry staining buffer. For serum collection, blood samples were left at room temperature for 30 minutes, centrifuged at 16,000×g for 20 minutes, and then collected and stored at −20° C. until analysis.

Bronchial alveolar lavage (BAL) fluid was collected. Briefly, the tracheae were cannulated with a 22-gage catheter tube (attached to a 5 cc syringe) and then washed once with 1 mL of sterile PBS. Samples were stored at −20° C. until analysis. For preparation of cells from lungs and spleens, these organs were harvested after the collection of BAL fluid, digested for 30 minutes at 37° C. in media containing 1 mg/mL Collagenase (Type 3; MP Biomedicals, Solon, Ohio) and 0.02 mg/mL DNase-I (MP Biomedicals), and then pressed through wire mesh to obtain a single cell suspension.

For preparation of cells from lungs, spleens, and lung draining lymph nodes (dLN), these organs were harvested after the collection of BAL fluid and digested for 30 minutes at 37° C. in media containing 1 mg/mL Collagenase (Type 3; MP Biomedicals, Solon, Ohio) and 0.02 mg/mL DNase-I (MP Biomedicals). Lungs and spleens were then pressed through wire mesh to obtain a single cell suspension. Draining lymph nodes were processed between two frosted microscope slides to obtain a single cell suspension. Preparation of cells from nasal tissue was performed as described in Pizzolla et al., *Resident memory CD8(+) T cells in the upper respiratory tract prevent pulmonary influenza virus infection*. Sci Immunol, 2017. 2(12). Briefly, a single cut along the vertical plane of the skull was performed to expose the nasal tissue. Forceps were used to scrape out the tissues and small bones from both sides of the nasal passages. Both bones and tissues were digested for 60 minutes at 37° C. in media containing 1 mg/mL Collagenase (Type 3; MP Biomedicals, Solon, Ohio) and 0.02 mg/mL DNase-I (MP Biomedicals). Tissue and bones were then strained through a 100 µm filter to obtain a single cell suspension.

Nanovax R848 Vaccination and Tissue Preparation.

Prior to i.n polyanhydride nanoparticle vaccinations, mice were anesthetized with isoflurane. For vaccinations utilizing Nanovax-R848, mice received one dose of 500 µg of Nanovax-R848 (1% HA, 1% NP, and 2% R848) i.n. in 50 µL of PBS followed by a boost of 500 µg of Nanovax-R848 at day 14. On day 25 post initial vaccination, sells were harvested from the nasal tissues, lung, and lung draining lymph nodes.

IAV-Specific Whole Virus ELISAs.

Total IAV-specific IgG and IgA antibody against whole A/Puerto Rico/8/34 live virus was measured as previously described (36). Briefly, wells were coated with ~3.2×10$^5$ TCIU$_{50}$ of virus, blocked with 1% bovine serum albumin, washed, and then blotted dry. Serum or BAL samples were added to the top well in triplicate at a 1:50 or 1:4 dilution in 200 µL/well, respectively. Samples were serially diluted at 1:2 and incubated at 37° C. for two hours. Plates were washed, blotted dry, and then IAV-specific antibody was detected using the following antibodies: biotin-labeled goat anti-mouse IgA (Southern Biotechnology Associates, Birmingham, Ala.); biotin-labeled AffiniPure goat anti-mouse IgG, Fc fragment specific (Jackson Immunoresearch Laboratories) followed by alkaline phosphatase-streptavidin (Invitrogen, Carlsbad, Calif.) and 2 mg/mL phosphatase substrate (Sigma-Aldrich, St. Louis, Mo.). Optical densities were measured at 405 nm using SpectraMax M5 Multi-mode microplate reader from Molecular Devices (Sunnyvale, Calif.).

Hemagglutination Inhibition Assay.

Hemagglutination inhibition (HAI) assays using mouse serum and BAL. Briefly, sera and BAL were inactivated by heating at 56° C. for 30 minutes and then absorbed in a chicken red blood cell (CRBC) suspension for 30 minutes at different concentrations:serum was absorbed in 1% CBRC at 1:5 and BAL was absorbed in 10% CBRC at 1:2. CBRCs were pelleted and both sera and BAL were serial diluted in 96-well round-bottom plates that were then incubated with four hemagglutination units of stock virus per well for 30 minutes. Each well then received 1% CBRC suspension and HAI titer was measured after a 30-minute incubation.

Antibody Staining for Flow Cytometry.

Single-cell suspensions (1×10$^6$ cells) from lungs were blocked with 2% rat serum for 30 minutes at 4° C. Following blocking, cells were stained with the following antibodies: rat anti-mouse CD4 (GK1.5; BioLegend), rat anti-mouse CD8a (53-6.7; BioLegend), rat anti-mouse CD49d (R1-2, BioLegend), rat anti-mouse CD11a (M17/4; BD Biosciences, San Jose, Calif.), rat anti-mouse CD103 (M290; BD Biosciences), rat anti-mouse CD69 (H1.2F3; eBioscience), and rat anti-mouse CD127(A7R34; BD Biosciences) to identify CD4 and CD8 T cell subsets. Antigen experienced T cells were identified via expression of surrogate markers. Briefly, CD11a$^{hi}$CD49d$^{pos}$ expression was utilized to identify antigen-experienced CD4 T cells, while CD11a$^{hi}$CD8α$^{lo}$ expression was utilized to quantify antigen-experienced CD8 T cells. To identify B cell subsets, cells were stained with rat anti-mouse CD19 (1D3; BD Biosciences), rat anti-mouse B220 (RA3-6B2; BioLegend), rat anti-mouse IgM (B7-6), and FITC-conjugated peanut agglutinin (PNA; Vector Laboratories, Burlingame, Calif.). Cells were then fixed with BD FACS™ Lysing Solution per manufacturer's instructions and resuspended in PBS. Data were acquired on a LSRII (BD Biosciences) and analyzed using FlowJo software (Tree Star, Ashland, Oreg.).

Statistical Analysis.

Experiments were repeated at least twice unless noted otherwise. Comparisons between two groups was performed with a two-tailed student's t-test. Comparisons between more than two groups at different time points were analyzed using two-way ANOVA with Holm-Sidak's multiple comparison post-hoc test. For comparisons between more than two groups at a single time point, a D'Agostino and Pearson normality test was performed to establish normality. Data that failed normalcy were analyzed using a Kruskal-Wallis ANOVA with a Dunn's multiple comparison post-hoc test. Data that passed normalcy were analyzed using a one-way ANOVA with a Tukey's multiple comparison post-hoc test. A P-value≤0.05 was considered significant.

Results.

IAV-Nanovax Induces Lung-Resident GC B Cells and IAV-Specific Antibody Responses In order to design an IAV vaccine that provides optimal protection by inducing long-lived local (i.e., lungs) and systemic immune responses, we made use of our CPTEG:CPH polyanhydride nanovaccine platform. Our previous studies have shown that a 20:80 CPTEG:CPH copolymer-based nanoparticle formulation is an effective delivery vehicle for IAV antigens and generation of systemic immune responses when given s.c. Therefore, in order to generate both lung-focused as well as systemic immunity, we designed an i.n. vaccine (IAV-nanovax) consisting of 20:80 CPTEG:CPH nanoparticles encapsulating 5 µg of both IAV HA and NP proteins [source A/Puerto Rico/8/34 (H1N1)] along with a 10 µg CpG oligo (ODN 1668) that is known to induce cross-presentation by dendritic cells.

The HA protein was included as it is a primary component of current vaccination strategies and is a focus of neutralizing antibody responses. In addition, NP protein was incorporated as it has been shown to drive NP-specific T cell responses that provide protection against heterologous infection as well as induce non-neutralizing antibody responses that facilitate more rapid T cell responses upon subsequent exposures. These nanoparticles were then administered i.n. in water along with 2.5 µg of free HA and NP proteins in a prime+boost regimen (Vela Ramirez et al., *Polyanhydride Nanovaccines Induce Germinal Center B Cell Formation and Sustained Serum Antibody Responses*. J Biomed Nanotechnol (2016) 12(6):1303-11. Epub 2016/06/21. PubMed PMID: 27319223; Ross et al., *Combination nanovaccine demonstrates synergistic enhancement in efficacy against influenza*. ACS Biomater Sci Eng (2016) 2(3): 368-74. doi: 10.1021/acsbiomaterials.5b00477.) has shown that the additional soluble antigen together with the nanovaccine during a prime+boost vaccination enhanced the immune response and protection following subcutaneous vaccination.

Figure 8:
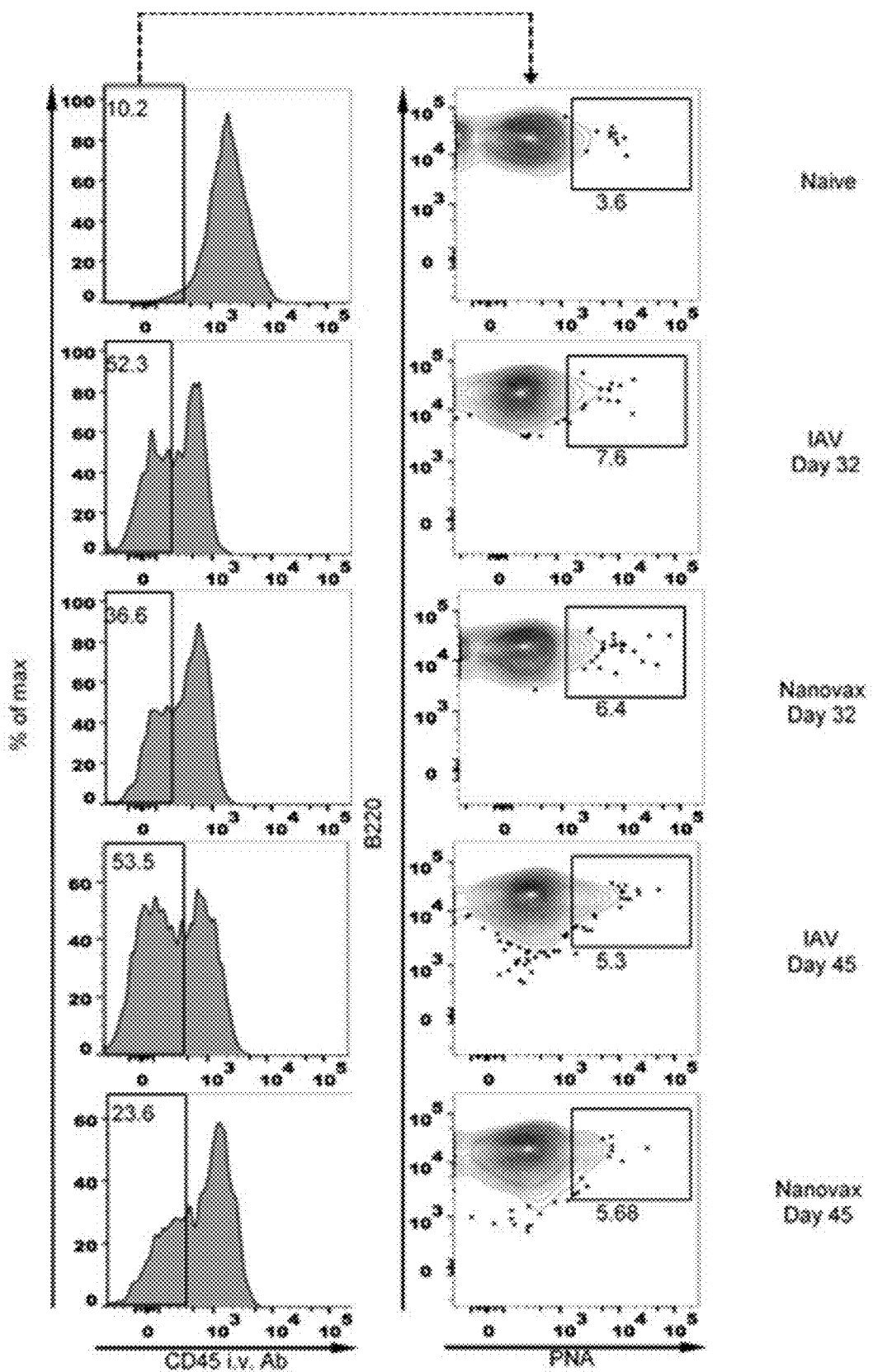
FIG. 8 illustrates lung resident GC B cell response gating strategy. C57BL/6 mice were challenged i.n. with 110 TCIU of A/Puerto Rico/8/1934, prime+boost vaccinated i.n. with IAV-nanovax or left unchallenged/unvaccinated (naïve). At 32 and 45 days post challenge/vaccination, mice received fluorophore conjugated anti CD45.2 monoclonal antibody intravenously (i.v.) 3 minutes prior to harvesting the lungs. Lung resident B cells (CD19+B220+, left column) were gated as CD45 i.v.Abneg. Lung resident GC B cells CD19+B220+CD45i.vAbnegPNApos were determined by subsequent PNA gating (right column). Flow plots are representative of 3 independent (Day 32) or 1 independent (Day 45) experiments with n=4 mice/group.

Since the generation of IAV-specific antibody responses are frequently used to determine IAV vaccine efficacy, we began by analyzing B cell responses in the lungs following i.n. IAV-nanovax vaccination and compared the response to mice i.n. infected with IAV (PR8; H1N1), mice i.m. vaccinated with IIV, or mice that were left untreated (naïve). In order to distinguish between lymphocytes embedded in the lung interstitium from those in the vasculature, we utilized an in vivo fluorophore-conjugated antibody labeling technique (FIG. 8). To this end, mice were intravascularly (i.v.) infused prior to lung harvest with a fluorescent antibody to label B cells within the circulation (CD45i.v.Ab$^{pos}$) vs. those in the lung parenchyma (CD45i.v.Abneg) (FIG. 8). Using this technique, we observed that total lung-resident B cells (CD19$^{pos}$B220$^{pos}$CD45i.v.Abneg) were significantly higher for IAV-infected and IAV-nanovax vaccinated mice compared to naïve and IIV controls at 32 and 45 days following infection/vaccination (FIGS. 1A, 1D).

Consistent with the increase in total numbers in IAV-infected and IAV-nanovax treated mice, lung-resident GC B cells (CD19$^{pos}$B220$^{pos}$CD45i.v.Ab$^{neg}$PNA$^{pos}$) were also significantly elevated at both time points (FIGS. 1B, 1E and FIG. 8). Similar trends were also observed in the lung draining lymph nodes. As GC B cell reactions result in class-switched B cells that produce higher affinity antibodies, we next compared the frequencies of IgM$^{neg}$ lung-resident GC B cells between IAV-infected and IAV-nanovax treated mice. As previously shown, IAV infection induces a substantial proportion of the GC response in the lungs to switch to IgG (IgM$^{neg}$IgG$^{pos}$) (36). Similar to IAV-infected mice, approximately 70% of lung resident GC B cells were IgM$^{neg}$ in IAV-nanovax mice, a finding consistent with a robust, mature GC response (FIGS. 1C, 1F). These results suggest that i.n. administration of IAV-nanovax induces lung-resident GC B cell responses capable of producing class-switched B cells to levels commensurate to those found in IAV-infected mice at 45 days following infection/vaccination.

Figure 2:
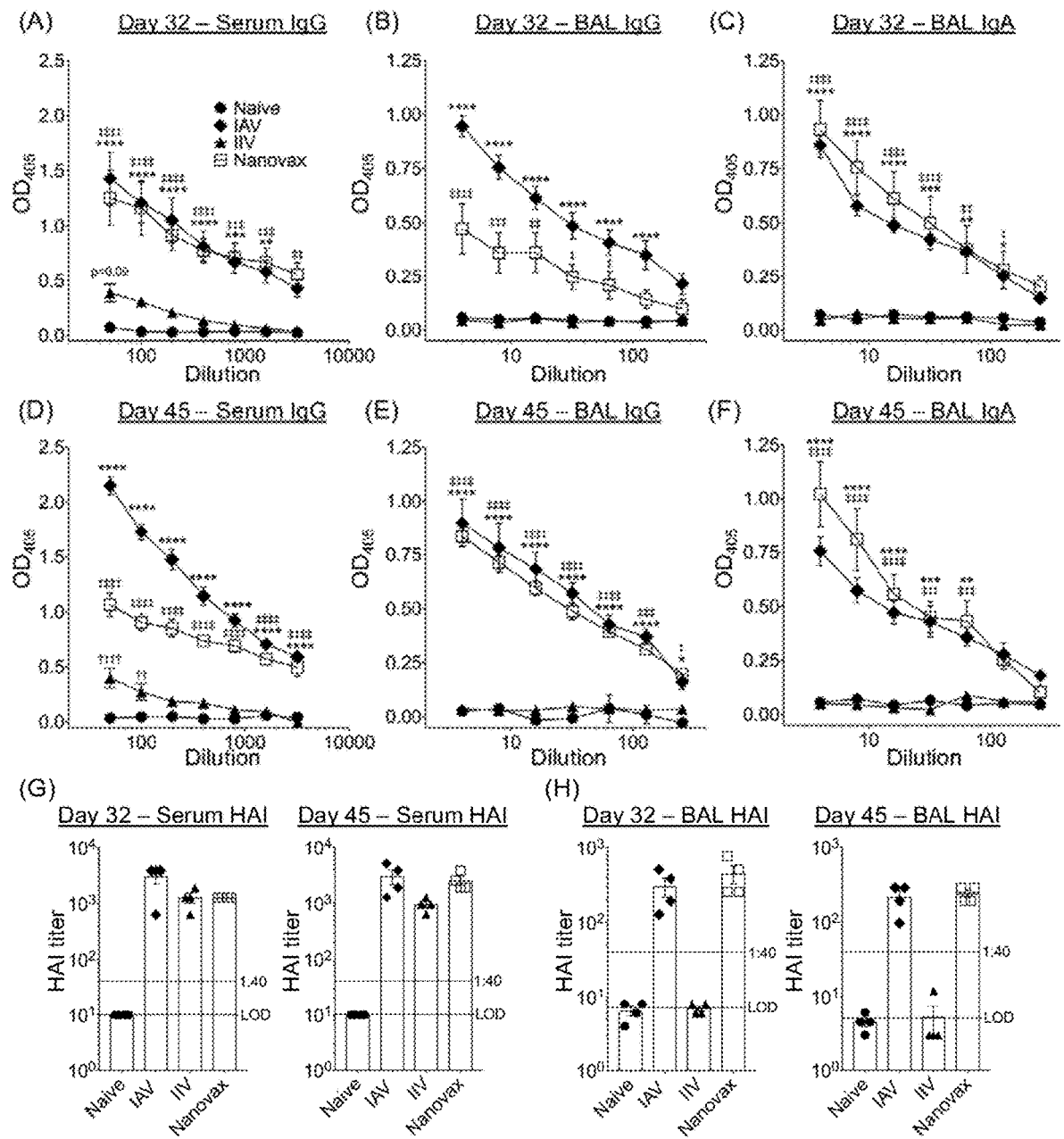
FIG. 2 illustrates the IAV-nanovax vaccination induces both lung and systemic IAV-specific antibody responses. C57BL/6 mice were vaccinated/infected as described in FIG. 1. At 32 and 45 days post challenge/vaccination, serum and BAL were collected. Total IAV-specific serum IgG (A, D), BAL IgG (B, E), and BAL IgA (C, F) were quantified by ELISA. Serum (G) and BAL (E) HAI levels were quantified. Error bars mean±s.e.m. LOD=limit of detection. Data are representative of three independent (A-C, G) or two independent (D-F, H) experiments with n=4-5 mice/group. IAV vs. naïve: *P<0.05, P<0.01, *P<0.001, ****P<0.0001; Nanovax vs. naïve: ‡P<0.05, ‡‡P<0.01, ‡‡‡P<0.001, ‡‡‡‡P<0.0001; IIV vs. naïve: ††P<0.01, ††††P<0.0001 (Two-way ANOVA with Holm-Sidak multiple comparisons test).

To determine if the observed B cell responses generated IAV-specific antibodies, we quantified total IAV-specific IgG and IgA antibody following infection or vaccination. As expected, IAV-specific IgG responses were detected locally (i.e., bronchoalveolar lavage (BAL)) and systemically (i.e., serum) in IAV-infected and IAV-nanovax vaccinated mice at 32 and 45 days following infection/vaccination (FIGS. 2A, 2B, 2D, 2E). Interestingly, serum levels of IAV-specific IgG antibodies were ~2-3× higher in animals after IAV-nanovax and IAV infection than in mice receiving IIV (FIGS. 2A, 2D). Mice receiving IIV also lacked robust IAV-specific IgG within the BAL as observed in IAV-nanovax and IAV infected mice (FIGS. 2B, 2E). This difference in measurable IAV-specific IgG within the BAL between IIV and IAV-nanovax is likely related to the lack of a local lung GC response in the IIV vaccinated mice (FIG. 1). Previous studies have demonstrated that IgA is present in the BAL after IAV infection. Consistent with this idea we found that both IAV-infection and IAV-nanovax, but not IIV, induced IAV-specific IgA levels in the BAL (FIG. 2C, 2F).

To determine the potential of these IAV-specific antibodies to contribute to protection from lethal dose IAV infections, we measured the capability of serum and BAL antibodies to inhibit IAV-hemagglutination. At 32 and 45 days post infection/vaccination, both IIV and IAV-nanovax vaccinated mice had serum hemagglutination inhibition (HAI) titers that were similar to IAV infected mice and well above the >1:40 mark that is associated with protection against subsequent IAV infection (FIG. 2G). However, only IAV infected and IAV-nanovax vaccinated mice possessed protective levels of HAI antibodies within the BAL (FIG. 2H). Altogether, these results suggest that i.n. administration of IAV-nanovax induces both local and systemic IAV-specific antibody responses capable of providing protection against IAV infection.

Figure 3:
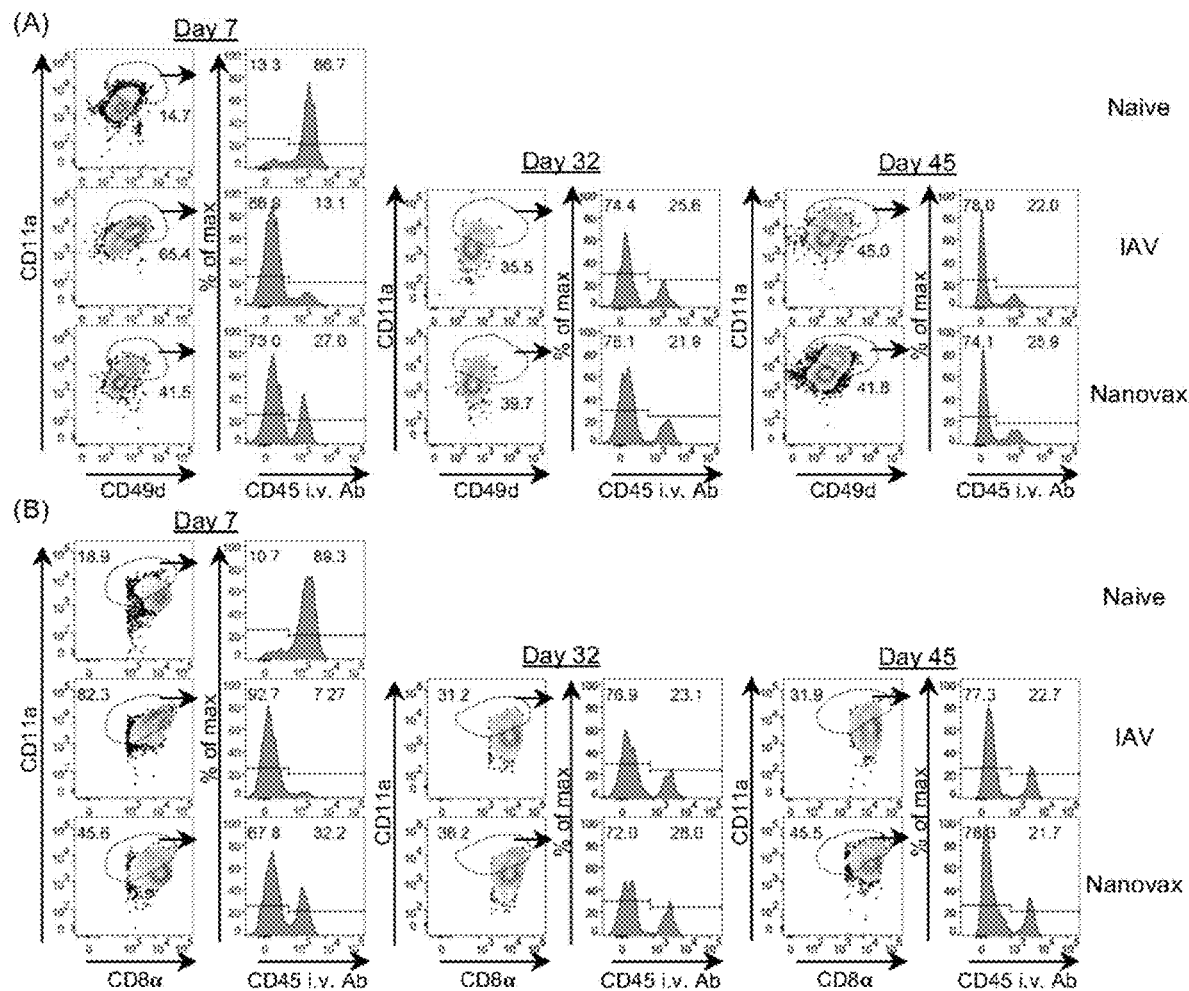
FIG. 3 illustrates IAV-specific lung-resident CD4 and CD8 T cell responses are induced following IAV-nanovax vaccination. C57BL/6 mice were vaccinated/infected as described in FIG. 1. At day 7, 32, and 45 post challenge/vaccination lungs were harvested. Representative gating strategies for (A) lung-resident AgExp CD4 T cells (CD11a$^{hi}$CD49d$^{pos}$CD45 i.v.Ab$^{neg}$) and (B) lung-resident AgExp CD8 T cells (CD11a$^{hi}$CD8α$^{lo}$CD45 i.v.Ab$^{neg}$). Numbers of (C-E) lung-resident AgExp CD4 and (F-H) lung-resident AgExp CD8 T cells were determined. Error bars mean±s.e.m. Data are from two pooled experiments with n=8 mice. *P<0.05, P<0.01, *P<0.001, ****P<0.0001 (Day 7; Kruskal-Wallis ANOVA with Dunn's multiple comparisons test. Day 32 and 45; One-way ANOVA with Tukey's multiple comparisons test).

IAV-Nanovax Generates Antigen Experienced CD4 and CD8 T Cell Responses within the Lungs Generation of GC B cell responses and class-switched antibodies are often associated with antigen-specific CD4 T cell responses. It has also been shown that IAV-specific CD8 T cells are important for control of IAV. Therefore, we determined the capacity of IAV-nanovax to elicit IAV-specific CD4 and CD8 T cell responses within the lungs. The CD4 T cell response to IAV has been shown to encompass a large number of epitopes, each only being expressed at low frequency. Thus, in order to not bias the response by examining a single epitope specificity we utilized a surrogate marker staining strategy. This strategy identifies total antigen-experienced T cells (FIGS. 3A, 3B), including those where epitopes have not been identified or are limited. Compared to naïve mice, IAV infection and IAV-nanovax vaccination generated an increased frequency of antigen-experienced CD4 T cells (AgExp CD4; CD4$^{pos}$CD11a$^{hi}$CD49d$^{pos}$) and antigen-experienced CD8 T cells (AgExp CD8; CD8$^{lo}$CD11a$^{hi}$) within the lungs at days 7, 32, and 45 (FIGS. 3A, 3B).

We further observed that a vast majority of these AgExp CD4 and AgExp CD8 T cells were resident within the lung tissue (CD45i.v.Ab$^{neg}$) based on in vivo antibody labeling in IAV-nanovax vaccinated mice, similar to that observed following IAV-infection (FIGS. 3A, 3B). Importantly, these lung-resident AgExp CD4 and CD8 T cells in IAV-nanovax vaccinated mice were found in higher numbers compared to naïve and IIV vaccinated mice at 7, 32, and 45 days post vaccination (FIGS. 3C-3H). Although numbers of lung-resident AgExp CD4 and CD8 T cells were higher early (day 7) in IAV-infected mice compared to IAV-nanovax mice (FIGS. 3C, 3F), IAV-nanovax was capable of inducing T cell responses of a similar magnitude to those observed in the IAV infected lung at later time points (FIGS. 3D, 3E, 3G, 3H)

Lung-Resident CD4 and CD8 T Cells Generated Following IAV-Nanovax Vaccination have a Memory Phenotype Recent studies have demonstrated that the presence of lung-resident memory T cells after IAV infection increases protection. Therefore, we next determined whether the robust lung-resident AgExp CD4 and CD8 T cell responses generated by IAV-nanovax vaccination shared phenotypic characteristics with canonical lung-resident memory T cells (Trm). In the IAV-infected lung, the expression of CD69 was prominent in lung-resident (i.e. CD45i.v.Ab$^{neg}$) AgExp CD4 T cells at 32 and 45 days following IAV infection, a change that is associated with establishment of lung-resident memory cells (FIG. 4A). This trend was also observed in IAV-nanovax vaccinated mice; however, IAV-nanovax induced a greater fraction of canonical CD69$^+$ AgExp CD4 Trm cells as well as a subset that co-expressed CD103 (FIGS. 4A, 4C). Nevertheless, both the CD69$^+$CD103$^+$ and CD69$^+$CD103$^-$ lung-resident AgExp CD4 T cell subsets were elevated in IAV-nanovax, but not IIV vaccinated, mice to levels equal to or higher than those observed in IAV-infected mice (FIG. 4C).

In contrast to lung Trm CD4 T cells, lung Trm CD8 T cells have been reported to co-express CD69 and CD103 (46). By day 32 following IAV-infection or IAV-nanovax vaccination, the fraction and number of CD69$^+$CD103$^+$ AgExp CD8 T cells resident within the lungs were significantly increased relative to naïve and IIV vaccinated mice (FIGS. 4B, 4D). Albeit the number of CD8 Trm were initially higher in IAV-infected mice, IAV-nanovax vaccinated mice exhibited similar CD8 Trm responses to IAV-infected mice by day 45 post infection/vaccination (FIG. 4D). Overall, these data suggest that IAV-nanovax vaccination induces CD4 and CD8 Trm responses of similar magnitudes to IAV infection.

IAV-Nanovax Provides Protection Against Homologous and Heterologous IAV Infections Given the robust pulmonary B and T cell responses we observed following IAV-nanovax vaccination, we next determined the potential of IAV-nanovax to circumvent IAV associated morbidity and mortality upon subsequent exposures. Further, since IAV-nanovax induced pulmonary CD4 and CD8 T cell responses within the lungs by day 7 post vaccination (i.e. prior to the boost, FIG. 3) we additionally compared protection after a prime only vs. a prime+boost vaccination schedule. Forty-five days after the initial vaccination, mice were challenged with a lethal dose of homologous IAV (A/Puerto Rico/8/34). As expected, naïve mice displayed substantial disease associated weight-loss (>20%), mortality (60%), and respiratory distress, as measured by increases in airway resistance (~6 Penh); however, mice that received either prime only or prime+boost IAV-nanovax administration exhibited reduced signs of morbidity and were completely protected against mortality (FIGS. 5A-5C).

Figure 9:
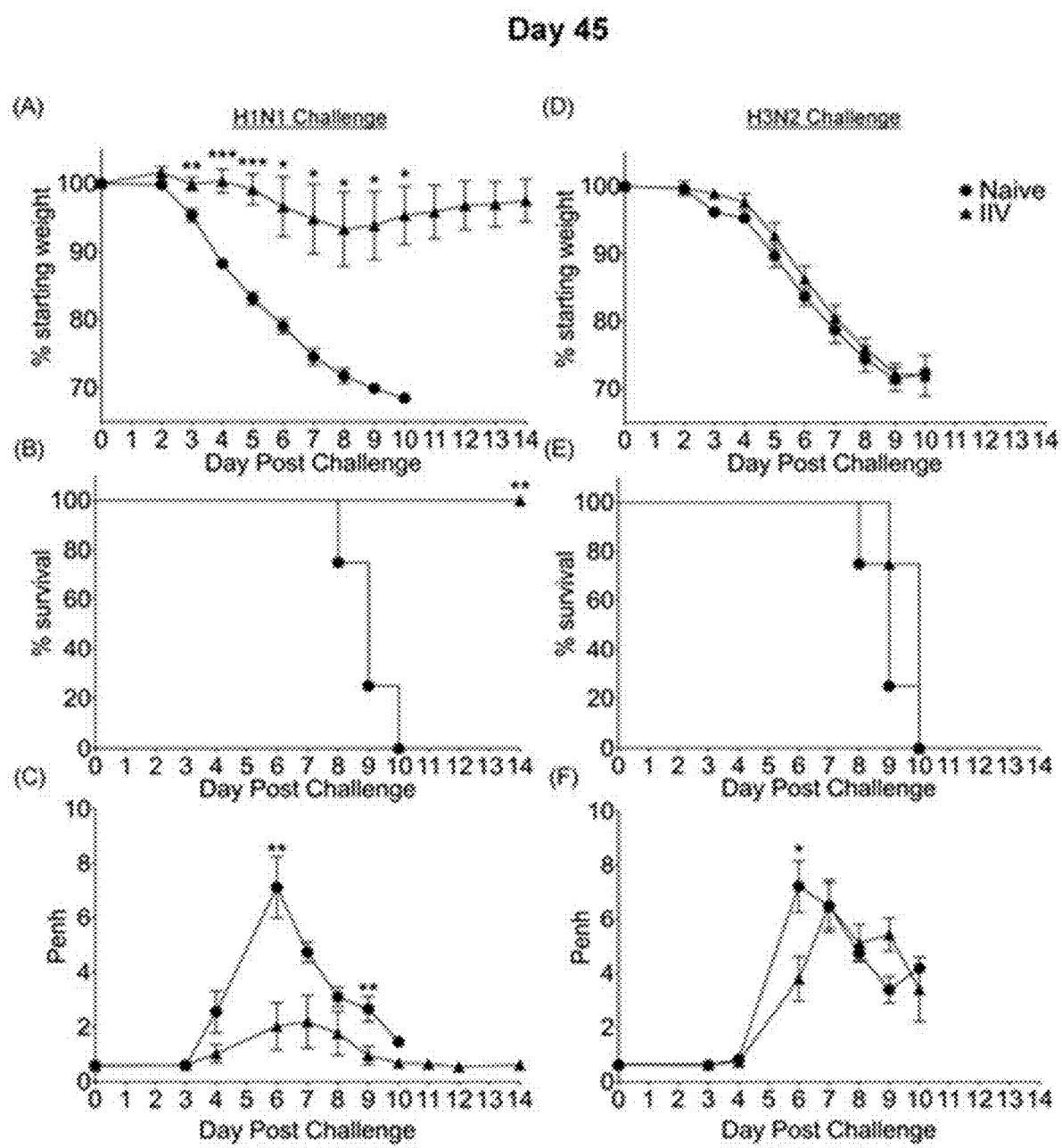
FIG. 9 illustrates intramuscular vaccination with IIV confers protection against subsequent homologous, but not heterologous, IAV infection. C57BL/6 mice received two-doses i.m. of IIV separated by 14 days or were left unvaccinated (naive). Forty-five days following the initial vaccination, mice were challenged with a (A-C) 1108 TCIU dose of A/Puerto Rico/8/1934 (H1N1) or (D-F) a 390 TCIU dose of A/Hong Kong/1/1968 (H3N2). Morbidity and mortality were measured by daily weight loss (A, D) and survival (B, E). (C, F) Penh was recorded daily as a measurement of lung function (airway resistance). Error bars mean±s.e.m. Data are representative of one independent experiment with n=5 mice/group. (A, C, D, E) *P<0.05, P<0.01, *P<0.001 (Two-way ANOVA with Holm-Sidak multiple-comparison test). (B, E) **P=0.01 (Mantel-Cox Log rank test).
Figure 10:
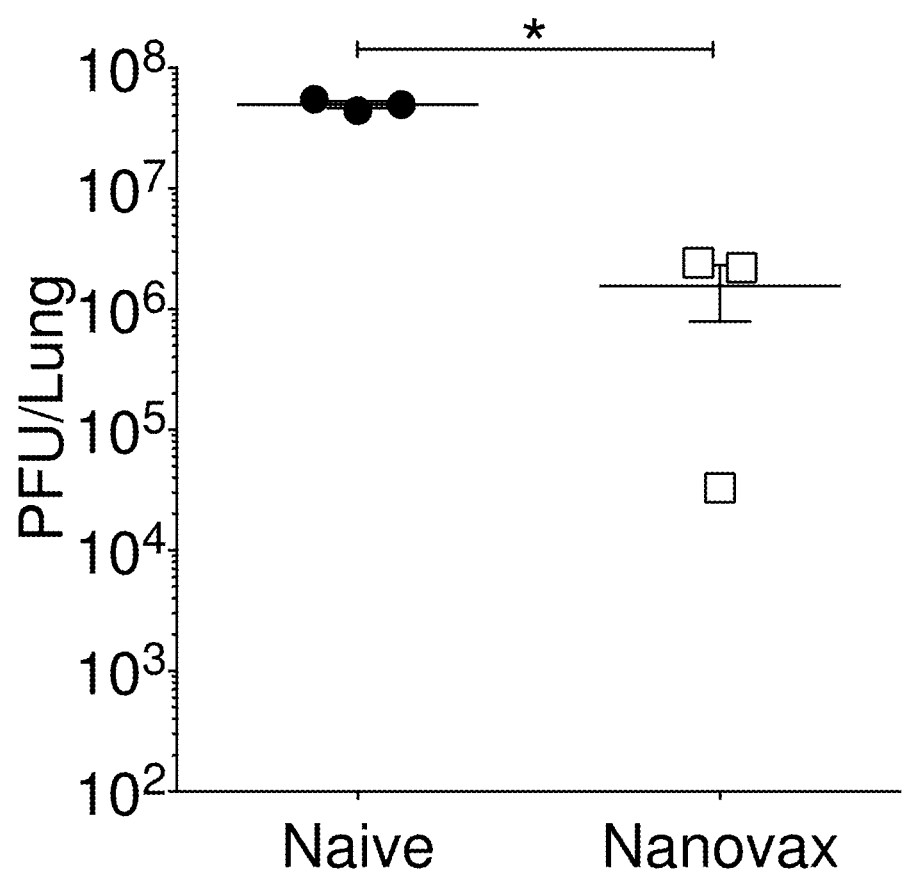
FIG. 10 illustrates vaccination with IAV-nanovax reduces viral titers within the lungs following challenge with homologous IAV. C57BL/6 mice received an i.n. prime+boost vaccination of IAV-nanovax or were left unvaccinated. 45 days after the initial vaccination they were challenged, as in FIG. 1 with a 1108 TCIU dose of A/Puerto Rico/8/1934 (H1N1). At 3 days post infection, virus titers in lung homogenates were measured by plaque assays. *P≤0.05 (two-tailed t test). Data are representative of 3 independent plaque assays with n=3 mice/group.

This alleviation of disease is commensurate to IIV vaccinated mice as similar trends of reduced morbidity and mortality were also observed for IIV prime+boost vaccinated mice compared to naïve (FIG. 9A-9C). Strikingly, IAV-nanovax prime+boost mice exhibited little to no weight loss or increases in Penh demonstrating that this strategy provides more robust protection compared to prime only mice (FIGS. 5A, 5C). Consistent with this disease amelioration, the IAV-nanovax prime+boost mice had significantly reduced lung viral titers three days following challenge indicating early control of viral replication (FIG. 10).

Since IAV-nanovax generated robust CD4 and CD8 Trm responses and recent studies have emphasized the importance of lung-resident CD4 and CD8 memory T cells in providing protection against subsequent heterologous IAV infections, we next determined if IAV-nanovax vaccination could confer protection against a heterologous IAV challenge. To this end, prime only and prime+boost IAV-nanovax vaccinated mice were challenged with a lethal dose of a mouse-adapted heterologous strain of IAV (A/Hong Kong/68, H3N2). Early (days 1-5) following challenge, IAV-nanovax vaccinated mice showed similar levels of weight-loss but reduced respiratory distress (Penh) compared to naïve mice (FIGS. 5D, 5F). Furthermore, while 100% of naïve mice succumbed to the highly stringent IAV challenge, both prime only (40%) and prime+boost (80%) IAV-nanovax mice were protected from mortality (FIG. 5E). Additionally, the protection mediated by IAV-nanovax appears durable as protection was still observed in mice challenged with homologous and heterologous virus at 100 days post vaccination (FIG. 6).

Figure 17:
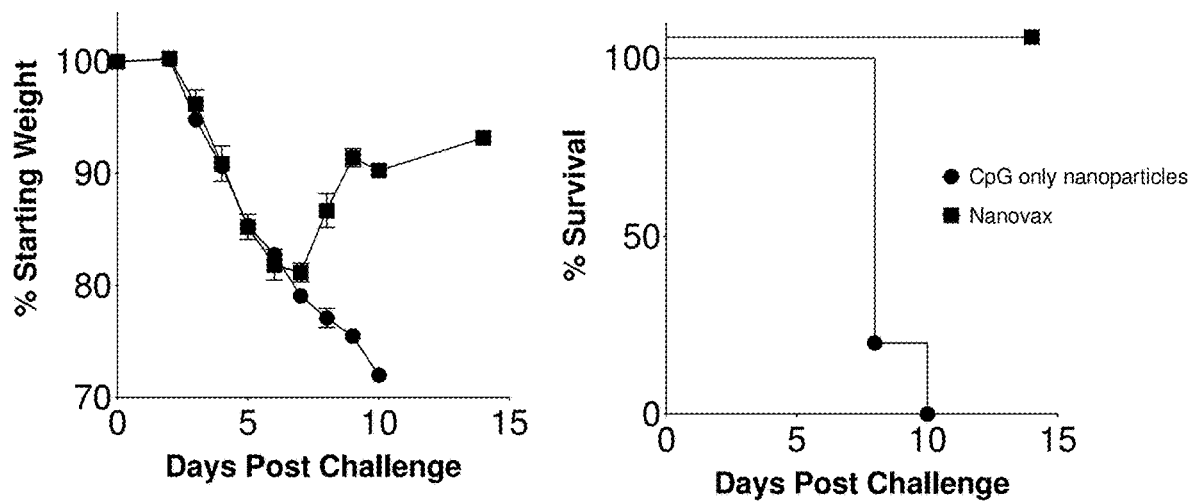
FIG. 17 illustrates that inclusion of IAV proteins in IAV-nanovax is necessary to achieve protection. C57BL/6 mice were vaccinated with ether IAV-nanovax or CpG only nanoparticles. On day 100 the mice were challenged with heterologous A/Hong Kong/1/1968 (H3N2) virus. Morbidity and mortality were measured by monitoring daily weight loss and survival.

The ability to IAV-nanovax to confer protection against heterologous virus challenge is likely due to the local lung adaptive immune response induced by IAV-nanovax as IIV vaccinated mice, which lack lung Trm (FIG. 3, 4), had limited to no protection from a heterologous challenge (FIG. 9D-9F). Furthermore, this protection appears to require adaptive immunity specific to influenza as mice vaccinated with polyanhydride particles that only contained CpG and no IAV protein (CpG Particles) showed no pulmonary B or T cell responses (FIG. 11A-11D) and were not protected upon subsequent viral challenge (FIG. 17). Overall, these data suggest that IAV-nanovax induces a long-lived adaptive immune response that may confer significant protection against subsequent homologous and heterologous IAV exposures.

Figure 11:
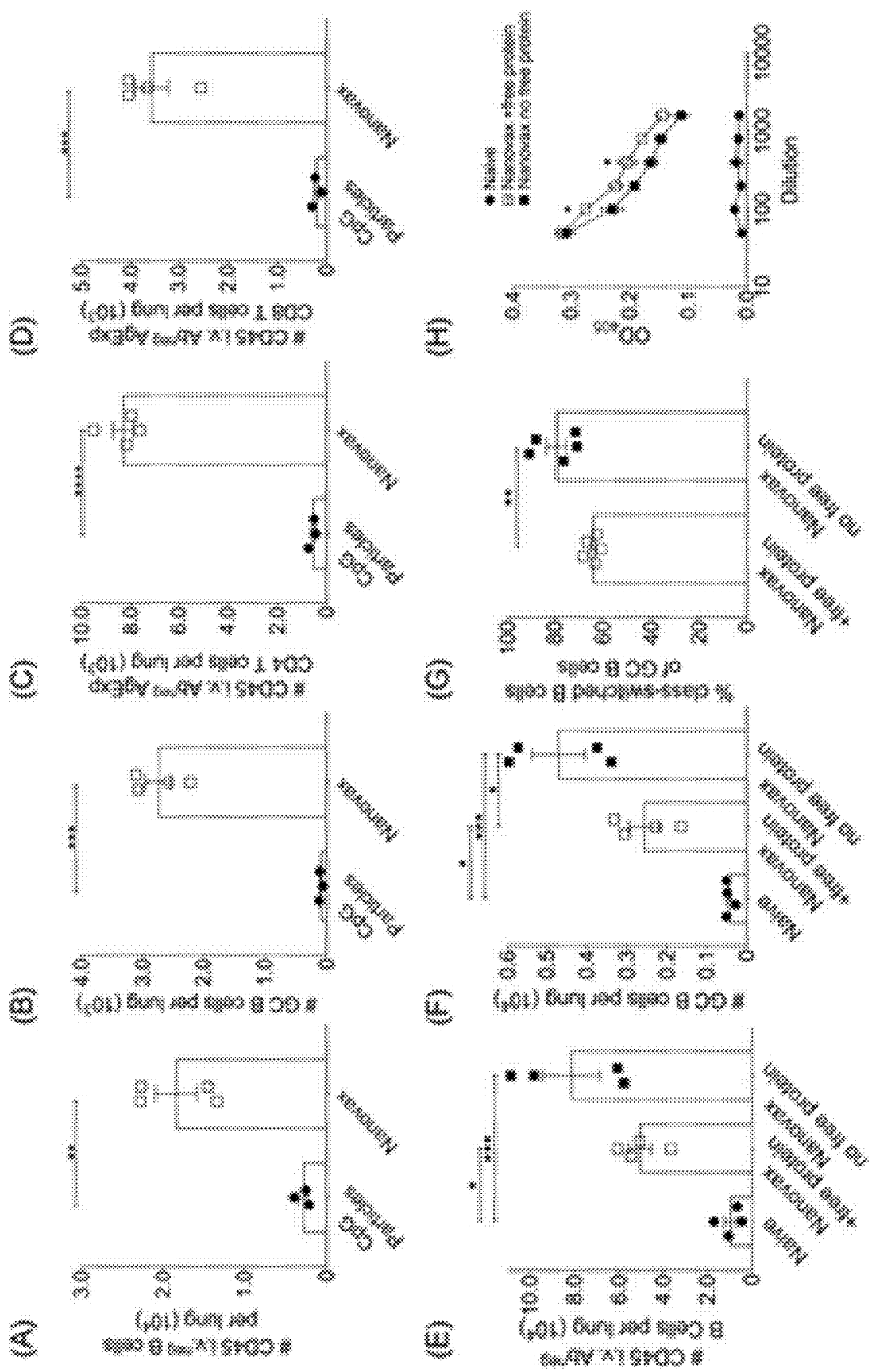
FIG. 11 illustrates immune response following vaccination with CpG only nanoparticles or IAV-nanovax without the free protein component. C57BL/6 mice received one dose i.n. of polyanhydride nanoparticles containing only CpG1668 (CpG Particles), two doses i.n. of IAV-nanovax (prime+boost) with or without free HA and NP protein or were left unvaccinated (naive). At 32 (E-L) or 45 (A-D, M-O) days following the initial vaccination (A,E) lung-resident B cells, (B,F) germinal center (GC) B cells, (G) class switched B cells, (C,I) lung-resident CD4 T cells, (D, K) lung-resident CD8 T cells, and Trm cells (J,L) were enumerated within the lungs. Serum was also collected and (H) total IAV-specific IgG was quantified by ELISA. A group of mice were also challenged with a (M-O) 1108 TCIU dose of A/Puerto Rico/8/1934 (H1N1). Morbidity and mortality were measured by daily weight loss (M) and survival (N). (O) Penh was recorded daily as a measurement of lung function (airway resistance). Error bars mean±s.e.m. Data are representative of one independent with n=4-5 mice/group. $*P<0.05, P<0.01, *P<0.001, ****P<0.0001$ (A-D: Two tailed student's t-test; E-G, I-L: One-way ANOVA with Tukey's multiple comparisons test; H, M, O: Two-way ANOVA with Holm-Sidak multiple comparisons test; N:Matel-Cox Log Rank Test).
Figure 12:
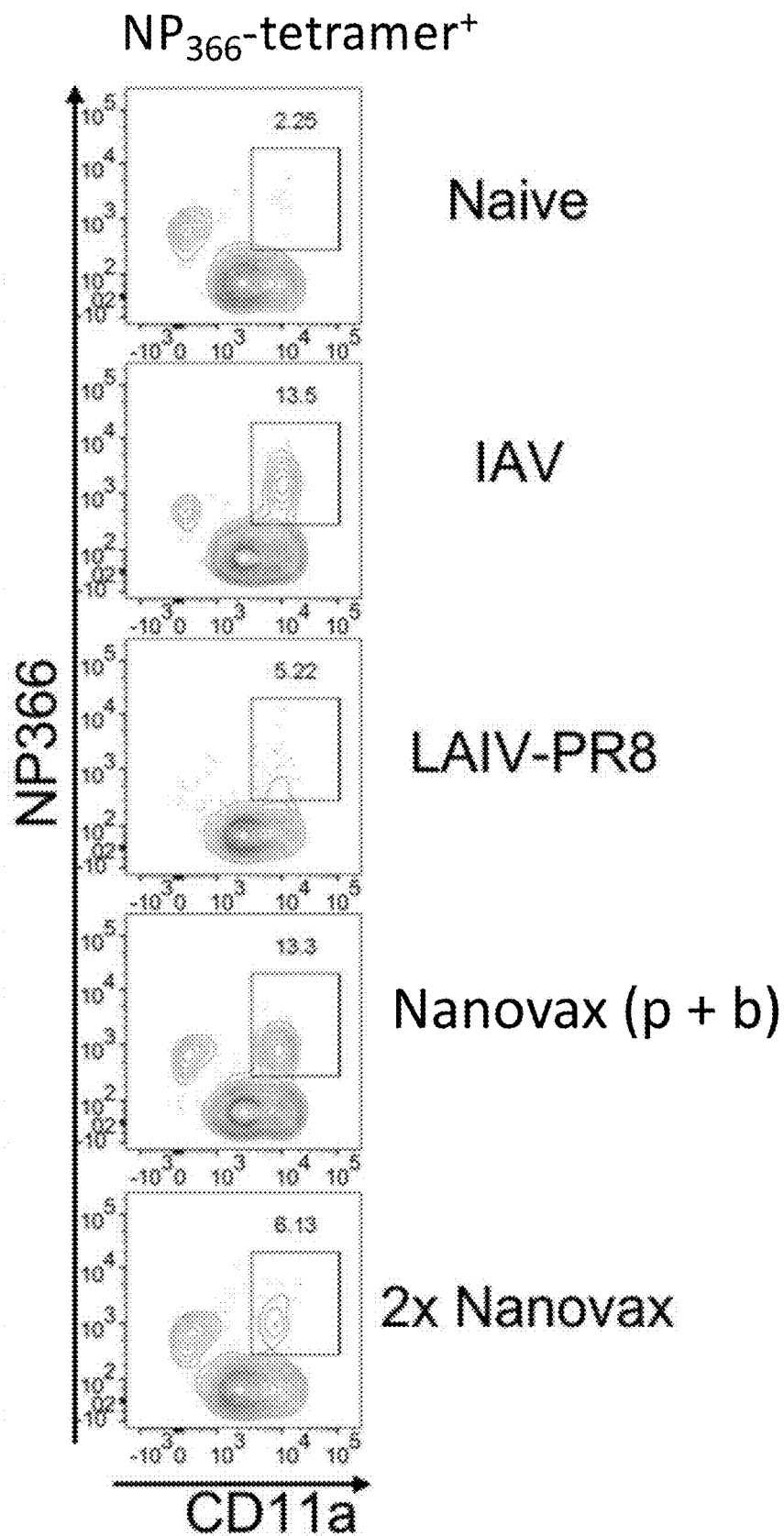
FIG. 12 illustrates IAV-specific nasal-resident CD8 T cell responses are induced following IAV-nanovax vaccination. C57BL/6 mice were vaccinated/infected with IAV, a PR8 based LAIV, IAV-Nanovax, or 2X-Nanovax formulation. At day 45 post challenge/vaccination nasal tissue was harvested and stained for expression of CD8, CD11a and binding of IAV-NP$_{366}$ tetramer. Shown are representative plots of CD8α$^+$ gated cells for the indicated vaccine/infection. The numbers within the panels show the % of CD11a$^+$NP$_{366}$-tetramer$^+$ cells among the gated CD8α$^+$ cells. These results demonstrate that IAV-nanovax induces IAV-specific CD8 T cell responses in the nasal passages in addition to lungs (data found in FIGS. 3-4, 11).
Figure 13:
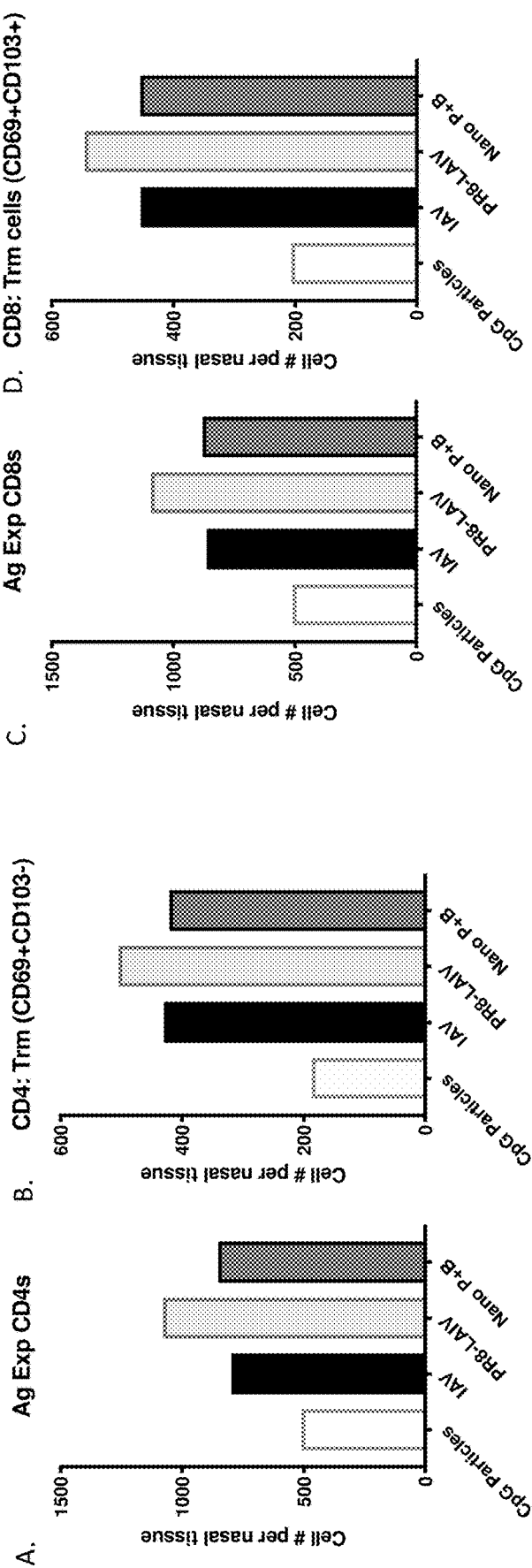
FIG. 13 illustrates IAV-specific nasal-resident CD4 and CD8 T cell responses are induced following IAV-nanovax vaccination. C57BL/6 mice were vaccinated/infected with IAV, a PR8 based LAIV, nanoparticles containing only CpG, or IAV-Nanovax. At day 45 post challenge/vaccination nasal tissue was harvested and stained for expression of CD4, CD8, CD11a, CD49d, CD69, and CD103. Three minutes prior to the harvest of the tissue, mice were administered anti-CD45 mAb to identify those cells within the blood vs cells within the tissues. Shown are the number of (A) total nasal-resident AgExp CD4 T cells (CD11a$^{hi}$CD49d$^{pos}$CD45 i.v.Ab$^{neg}$), (B) total nasal-resident AgExp Trm CD4 T cells (CD4$^+$CD11a$^{hi}$CD49d$^{pos}$CD45 i.v.Ab$^{neg}$CD69$^+$CD103$^-$), (C) nasal-resident AgExp CD8 T cells (CD11a$^{hi}$CD8α$^{lo}$CD45 i.v.Ab$^{neg}$), and (D) nasal-resident AgExp Trm CD8 T cells (CD11a$^{hi}$CD8α$^{lo}$CD45 i.v.Ab$^{neg}$ CD69$^+$CD1031. These results demonstrate that IAV-nanovax induces IAV-specific memory CD4 and CD8 T cell responses in the nasal passages in addition to lungs (data found in FIGS. 3-4, 11).
Figure 14:
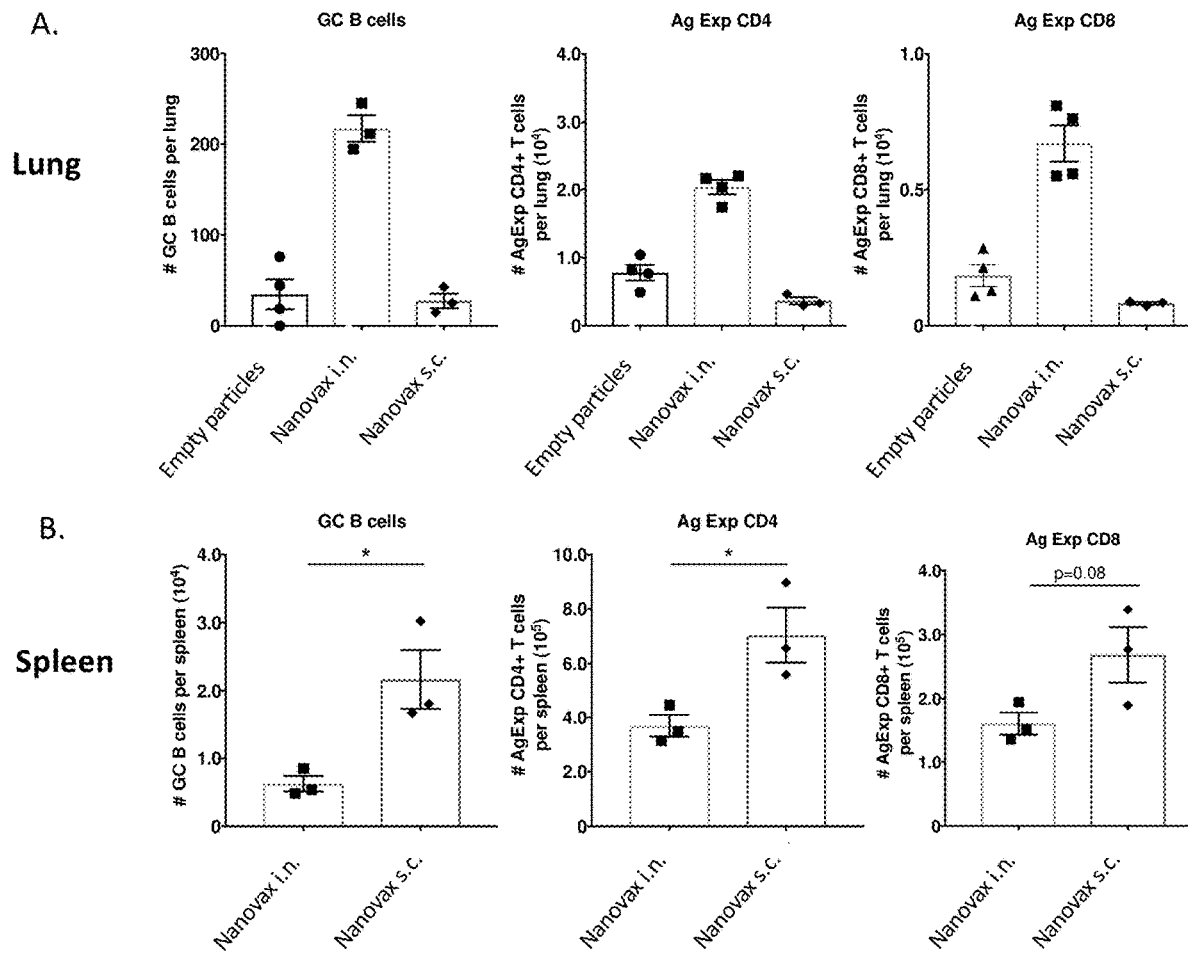
FIG. 14 illustrates intranasal (i.n.), but not subcutaneous (s.c.), administration of IAV-nanovax induces robust lung resident B and T cell immunity. C57BL/6 mice were vaccinated/infected with empty nanoparticles i.n., IAV-Nanovax i.n., or IAV-nanovax s.c. At day 45 post vaccination lungs and spleen were harvested and the cells were analyzed for expression of CD4, CD8, CD11a, CD49d, CD19, B220, and PNA. Shown in (A, B) is the number of germinal center B cells (CD19$^+$B220$^+$PNA$^+$), antigen-experienced (AgExp) CD4 (CD4$^+$CD11a$^{hi}$CD49d$^+$) or AgExp CD8 (CD8$^{lo}$CD11a$^{hi}$) T cells in the lungs (A) or spleen (B). While intranasal IAV-nanovax induces robust lung GC B cells, AgExp CD4, and AgExp CD8 T cells responses, s.c. administration does not. Both s.c. and i.n. administration induces GC B cells, AgExp CD4 T cell, and AgExp CD8 T cell responses in the spleen, with s.c. IAV-nanovax inducing a larger splenic response. Overall, these results demonstrate that i.n. IAV-nanovax administration induces both a local (i.e. lungs) as well as systemic (spleen) immune response and that i.n. administration is necessary to drive a robust adaptive immune response within the lungs.
Figure 15:
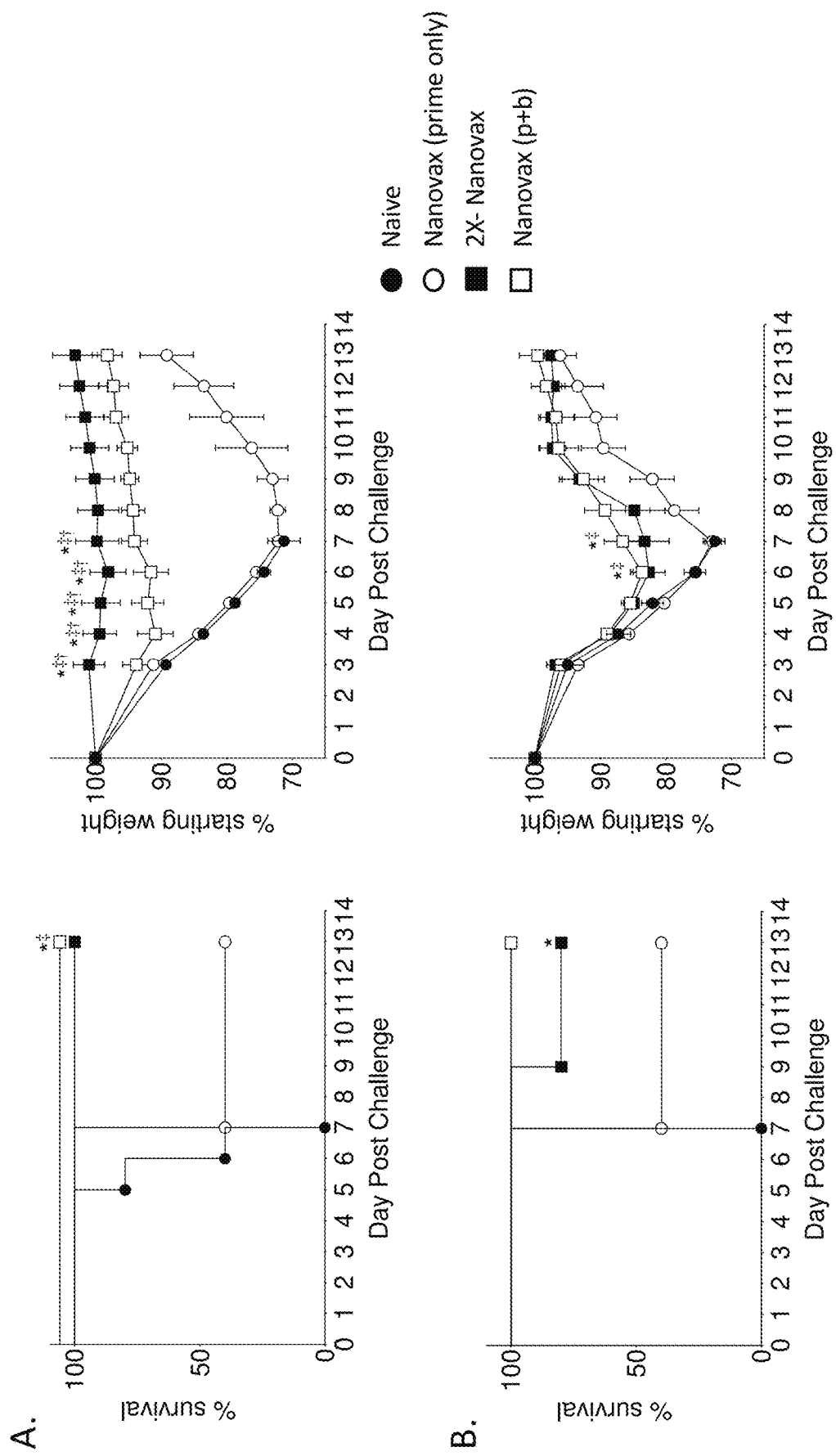
FIG. 15 illustrates IAV-nanovax (prime+boost) and 2X-IAV-nanovax (prime only) confer protection against subsequent homologous and heterologous IAV infection. C57BL/6 mice received one-dose i.n. of IAV-nanovax (prime only), two-doses i.n. of IAV-nanovax (prime+boost), one-dose i.n. of 2X IAV-nanovax (prime only) or were left unvaccinated (naive). Forty-five days following the initial vaccination, mice were challenged with a (A) 1108 TCIU dose of homologous A/Puerto Rico/8/1934 (H1N1) or (B) 390 TCIU dose of heterologous A/Hong Kong/1/1968 (H3N2). Morbidity and mortality were measured by daily weight loss and survival. Both IAV-nanovax (p+b) and 2X-IAV-nanovax (prime only) induce robust protection against both homologous and heterologous virus exposures. The 2X-nanovax results demonstrate that it is possible to achieve protection using a single i.n. vaccination without a boost using an IAV-nanovax formulation.
Figure 16:
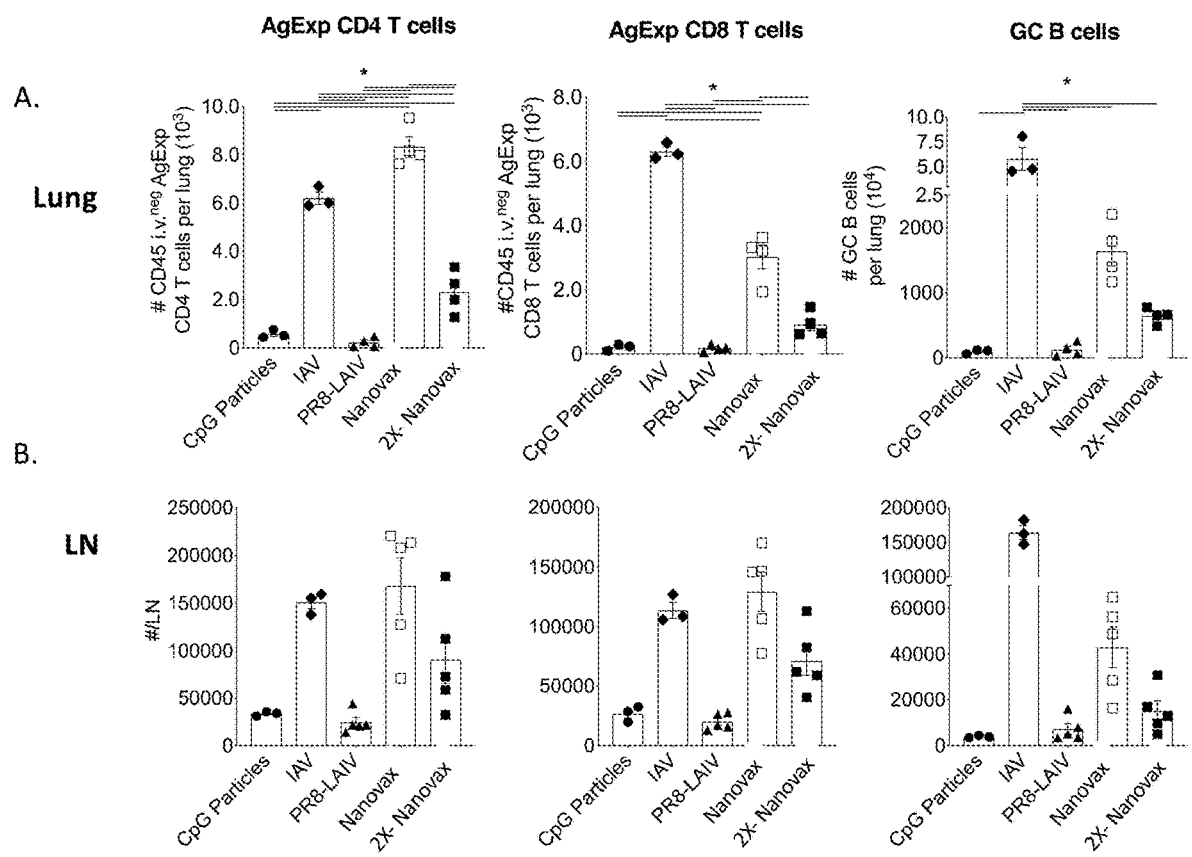
FIG. 16 illustrates that 2X IAV-nanovax induces B and T cell immunity in the lungs and lung draining lymph nodes. C57BL/6 mice vaccinated/infected with IAV, a PR8 based LAIV, nanoparticles containing only CpG, two-doses i.n. of IAV-nanovax (prime+boost, Nanovax), or one-dose i.n. of 2X IAV-nanovax (prime only, 2X-Nanovax). Forty-five days following the initial vaccination/infection, the lungs (A) and lung draining lymph nodes (B, LN) were harvested. The cells were then analyzed for expression of CD4, CD8, CD11a, CD49d, CD19, B220, and PNA. Shown are the number of germinal cell B cells (CD19$^+$B220$^+$PNA$^+$), AgExp CD4 (CD4$^+$CD11a$^{hi}$CD49d$^+$) or AgExp CD8 (CD8$^{lo}$CD11a$^{hi}$) T cells in the indicated tissue. While intranasal IAV-nanovax and 2X-IAV-nanovax induce GC B cell, AgExp CD4, and AgExp CD8 T cells responses in the lungs and lung draining lymph nodes, similar to IAV infection, LAIV and CpG only nanoparticles do not. This demonstrates that IAV-nanovax induces adaptive immune responses in the lungs that LAIV does not. Further the lack of immunity following the CpG only nanoparticles demonstrates the IAV-protein incorporated in the nanoparticles are necessary for the induction of the IAV-specific adaptive immune response. While the immune response generated after single administration of the 2X-Nanovax formulation is not as robust as after the IAV-nanovax (p+b) administration, it does induce influenza-specific adaptive immune responses and these responses are able to confer protection.

Further, we included a free antigen component in our vaccine as our prior results with s.c. vaccination had demonstrated that inclusion of this free antigen component enhanced immune responses and protection. In order to determine if the free antigen component was likewise required during i.n. vaccination, we next compared immune responses and protection in mice vaccinated with IAV-nanovax+/− the free IAV antigens. As shown in FIG. 11E-11L, when the immune response in the lungs was examined at 32 days post vaccination lung-resident B cell numbers, GC B cell numbers, the fraction of class-switched GC B cells, the number of lung-resident antigen-experienced CD4 and CD8, as well as CD4 and CD8 Trm cells were equivalent or increased when the free antigen component was not administered as part of the vaccine. Likewise, IAV-specific IgG antibody titers in the serum were similar. Finally, no differences were observed in the ability of the vaccine to confer protection against a subsequent lethal dose homologous IAV challenge when IAV-nanovax vaccines were administered with or without a free antigen component were compared (FIG. 11M-11O). Altogether these results suggest that a free antigen component is not required during i.n. IAV-nanovax vaccination to generate robust immunity and protection.

These results demonstrate the ability of IAV-nanovax to confer protection against IAV infections in an inbred C57BL/6 mouse model. The use of inbred models offers many advantages during the testing and design of vaccines, but these models do not represent the genetic diversity found in humans. Therefore, in order to determine if IAV-nanovax could likewise confer protection in outbred populations, we next i.n. vaccinated groups of outbred Swiss-Webster mice with IAV-nanovax. Groups of non-vaccinated mice were included as controls. These groups were then subsequently challenged on day 45 post vaccination with either lethal dose homologous (FIGS. 7A-7C) or heterologous (FIGS. 7D-7F) IAV. IAV-nanovax vaccination significantly reduced/ablated morbidity (weight loss, FIGS. 7A, 7D; Penh, FIGS. 7C, 7F) and protected from mortality (FIGS. 7B, 7E) upon subsequent challenges. Thus, these results demonstrate that IAV-nanovax is able to protect against subsequent homologous and heterologous IAV infections in a translational outbred model.

Discussion.

Figure 5:
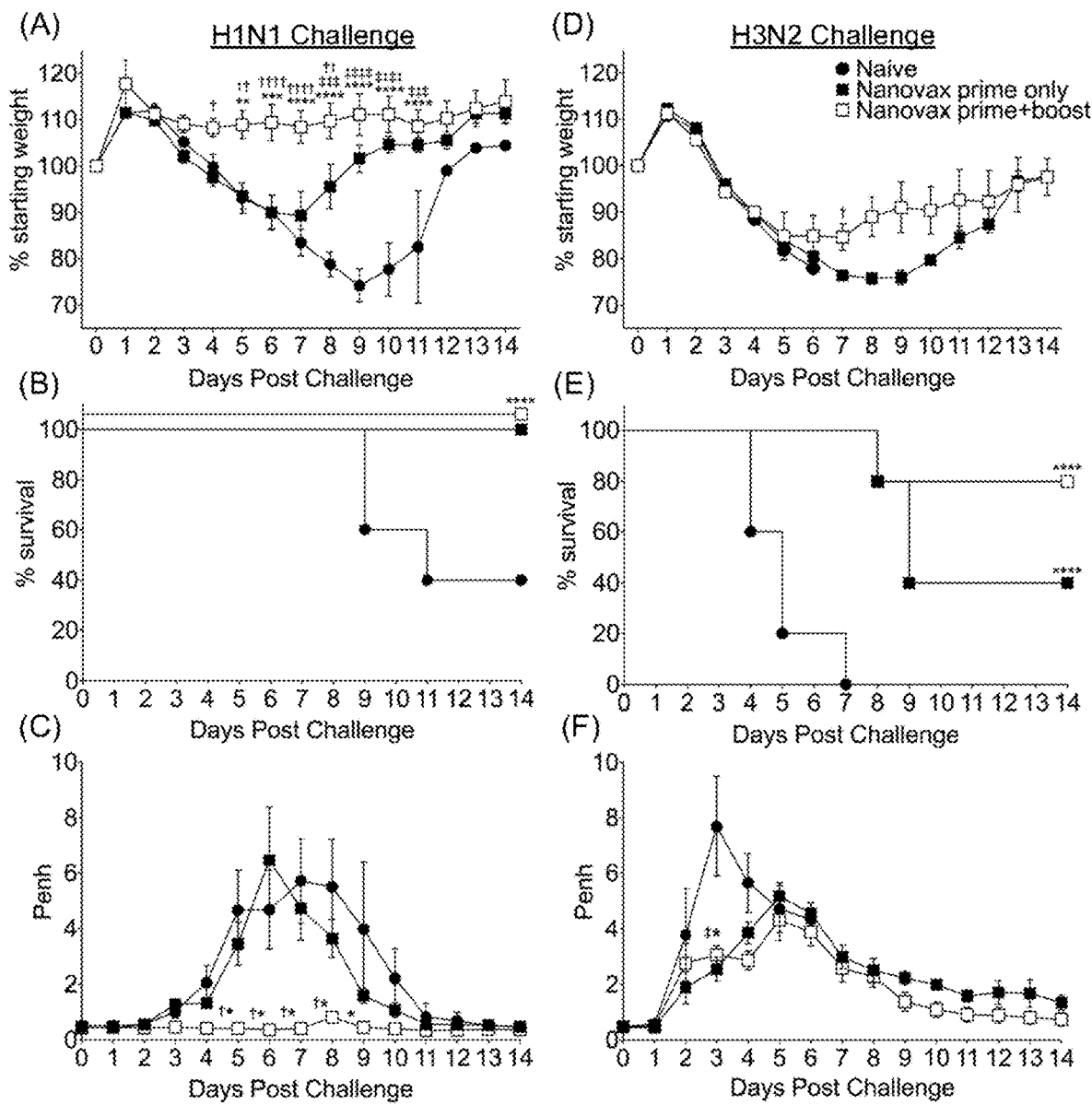
FIG. 5 illustrates IAV-nanovax confers protection against subsequent homologous and heterologous IAV infection. C57BL/6 mice received one-dose i.n. of IAV-nanovax (prime only), two-doses i.n. of IAV-nanovax (prime+boost), or were left unvaccinated (naive). Forty-five days following the initial vaccination, mice were challenged with a (A-C) 1108 TCIU dose of A/Puerto Rico/8/1934 (H1N1) or (D-F) 390 TCIU dose of A/Hong Kong/1/1968 (H3N2). Morbidity and mortality were measured by daily weight loss (A, D) and survival (B, E). (C, F) Penh was recorded daily as a measurement of lung function (airway resistance). Error bars mean±s.e.m. Data are representative of two independent (C, F) or three independent (A, B, D, E) experiments with n=5 mice/group. (A, C, D, F): Nanovax prime+boost vs. naïve: *P<0.05, P<0.01, *P<0.001, **P<0.0001; Nanovax prime only vs. naïve: ‡P<0.05, ‡‡‡P<0.001, ‡‡‡‡P<0.0001; Nanovax vs. IAV: †P<0.05, ††P<0.01, ††††P<0.0001 (Two-way ANOVA with Holm-Sidak multiple-comparison test). (B, E) **P=0.0001 to naïve (Mantel-Cox Log rank test).
Figure 6:
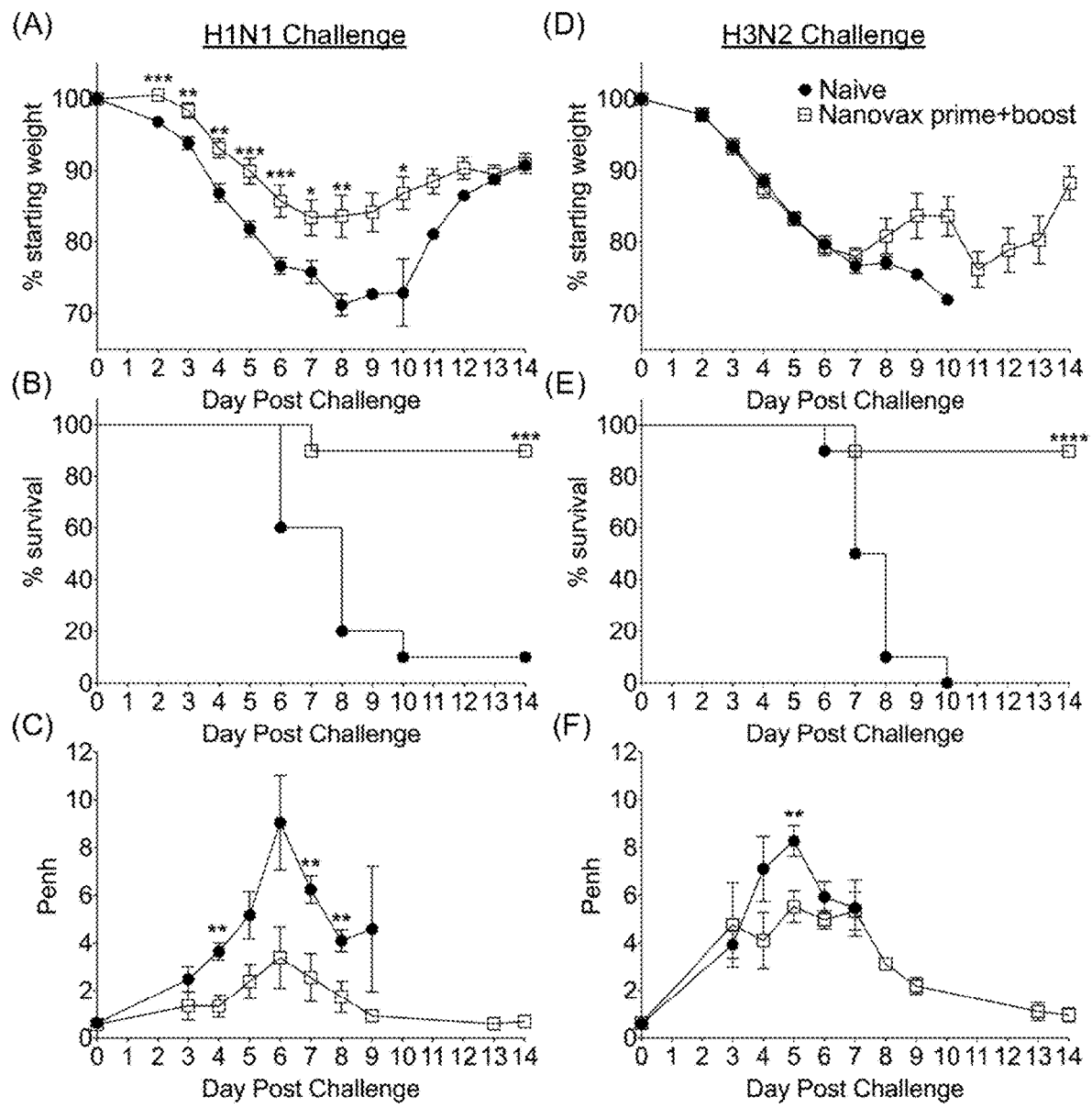
FIG. 6 illustrates homologous and heterologous protection mediated by IAV-nanovax is long-lived. C57BL/6 mice received two-doses i.n. of IAV-nanovax (prime+boost) or were left unvaccinated (naive). One-hundred days following the initial vaccination, mice were challenged with a (A-C) 1108 TCIU of A/Puerto Rico/8/1934 (H1N1) or (D-F) 390 TCIU of A/Hong Kong/1/1968 (H3N2). Morbidity and mortality were measured by daily weight loss (A, D) and survival (B, E). (C, F) Penh was recorded daily as a measurement of lung function (airway resistance). Error bars mean±s.e.m. Data are of two pooled experiments (A, B, D, E) with n=10 mice/group or representative of one independent experiment (C, F) with n=5 mice/group. (A, C, D, F) *P<0.05, P<0.01, *P<0.001 (Two-tailed student's t test). (B, E)*P<0.001, **P<0.0001 (Mantel-Cox Log rank test).
Figure 7:
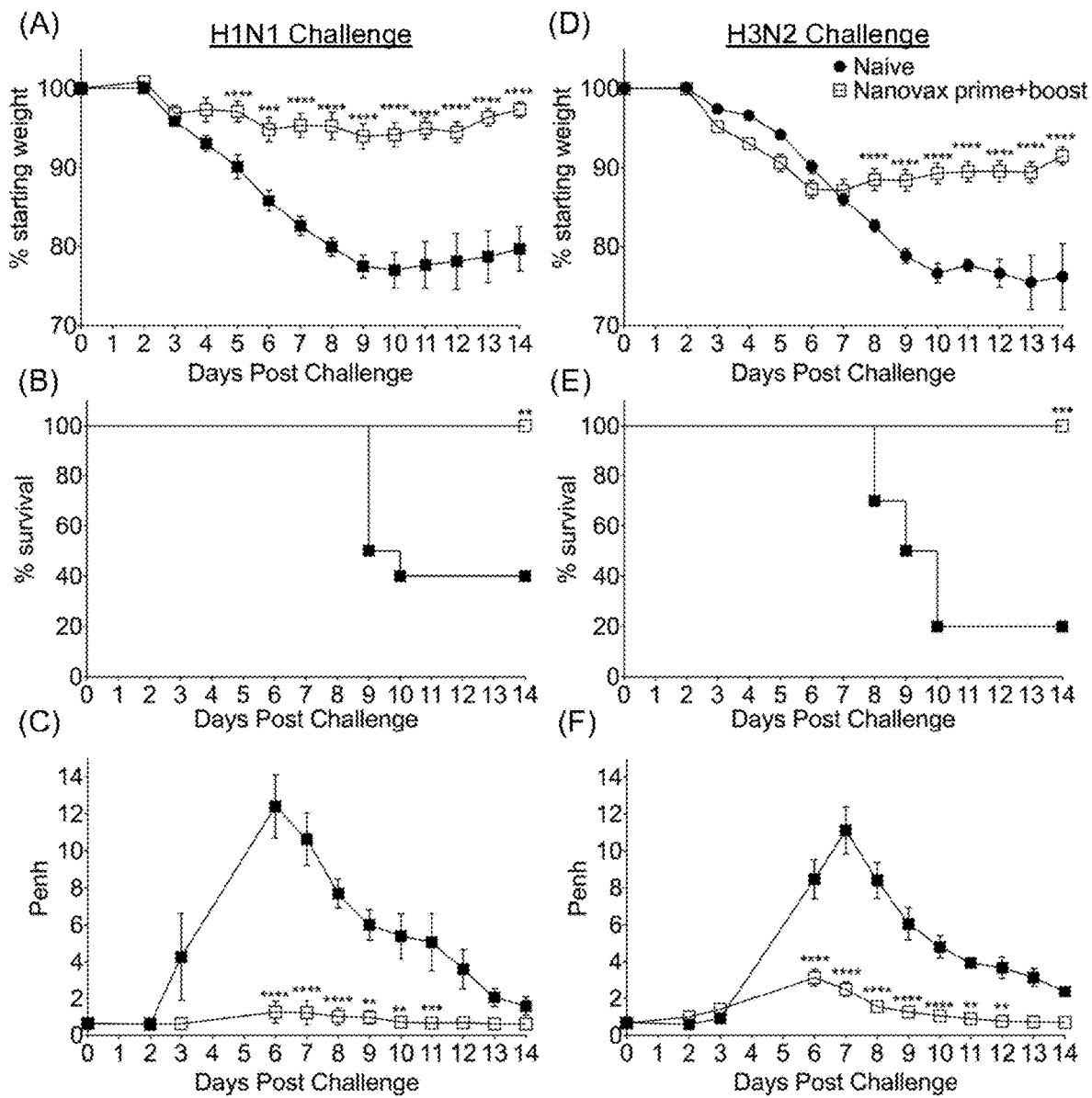
FIG. 7 illustrates IAV-nanovax confers protection against subsequent homologous and heterologous IAV infection in outbred mice. Outbred Swiss Webster mice received a prime+boost i.n. vaccination of IAV-nanovax without free protein or were left unvaccinated. Forty-five days following the initial vaccination, mice were challenged with a (A-C) 1108 TCIU dose of A/Puerto Rico/8/1934 (H1N1) or (D-F) 390 TCIU dose of A/Hong Kong/1/1968 (H3N2). Morbidity and mortality were measured by daily weight loss (A, D) and survival (B, E). (C, F) Penh was recorded daily as a measurement of lung function (airway resistance). Error bars mean±s.e.m. Data are representative of one independent with n=10 mice/group. (A, C, D, F) P<0.01, *P<0.001, **P<0.0001 (Two-way ANOVA with Holm-Sidak multiple-comparison test). (B, E) P<0.01, ***P<0.001 (Mantel-Cox Log rank test).

In the present study, we have demonstrated the efficacy of an i.n. administered CPTEG:CPH IAV-nanovax in producing IAV-specific immune responses and providing protection against subsequent homologous and heterologous IAV infections (FIGS. 5-7). While the protection provided by IAV-nanovax was found to be more robust after a prime+boost strategy, the prime only vaccination substantially reduced morbidity (FIGS. 5A, 5C) and completely prevented mortality (FIG. 5B) following a homologous IAV challenge. Likewise, the prime only vaccination reduced initial airway distress (FIG. 5F) and provided a significant level of protection from mortality during a lethal-dose heterologous IAV challenge (FIG. 5E).

This protection against homologous and heterologous virus appears to be long lasting as IAV-nanovax vaccination also conferred protection in mice challenged at 100 days post vaccination (FIG. 6). While the IAV-nanovax formulation tested herein contained only IAV HA and NP proteins, studies have demonstrated that immunity directed against additional IAV proteins such as NA and M1 can enhance protection. One of the benefits of our nanovaccine platform is the ability to easily "plug and play" new antigens within the formulation. Therefore, by incorporating IAV NA and M1 protein within future IAV-nanovax formulations we may be able to drive even more robust immunity and further improve protection against homologous and heterologous IAV infections.

Consistent with the ability to protect against homologous virus challenge, intranasal vaccination with IAV-nanovax induced IAV-specific class-switched GC B cell responses that were resident in the lung as well as robust local (IgG and IgA) and systemic (IgG) IAV-specific antibodies (FIG. 1, FIG. 2). However, at some time points we did observe reduced IAV-specific IgG in IAV-nanovax vaccinated mice compared to IAV infection (day 45 serum, day 32 BAL, FIGS. 2B, 2D). This reduction could be related to additional antigens available for targeting following IAV infection since IAV-nanovax only contains IAV HA and NP proteins. Consistent with this idea, HAI titers in the serum and BAL following IAV-nanovax were similar to those observed for an IAV infection and well above the 1:40 HAI titer associated with protection (43) suggesting that HA-specific antibodies are equal.

Based on the observed protective ability of Trm against IAV, it has recently been suggested that a "universal" vaccine against IAV should induce such T cell responses in order to offer the greatest level of protection. Importantly, analysis of the lungs after IAV-nanovax vaccination found the presence of IAV-specific CD4 and CD8 T cells. These IAV-specific CD4 and CD8 T cells were within the lung parenchyma based on CD45 i.v.Ab exclusion staining (FIG. 3) and expressed markers consistent with the canonical tissue-resident memory phenotypes. Lung-resident memory CD4 T cells are primarily identified by CD69 expression following infection or vaccination. While we observed $CD69^+CD103^-CD4$ Trm subset within the lungs of IAV-nanovax vaccinated mice, we unexpectedly observed a small proportion of $CD69^+CD103^+$ CD4 T cells as well (FIG. 4A, 4C). Although this $CD4^+CD69^+CD103^+$ resident memory phenotype has not been well characterized, a study has reported this subset within the skin. What role these $CD69^+CD103^+$ CD4 T cells may play in protection against subsequent IAV infections remains to be determined.

Figure 4:
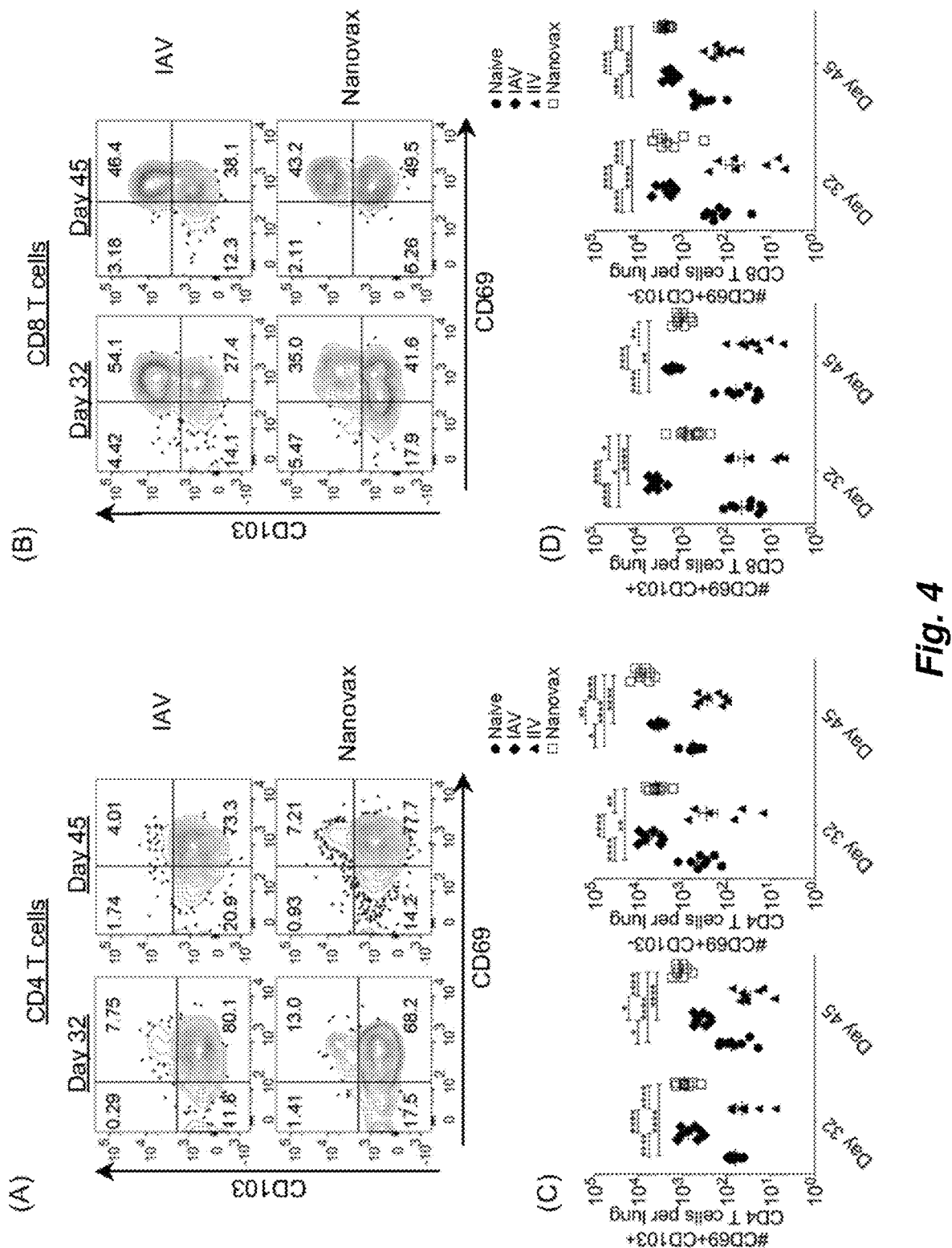
FIG. 4 illustrates vaccination with IAV-nanovax induces IAV-specific tissue-resident memory CD4 and CD8 T cells within the lungs. C57BL/6 mice were vaccinated/infected as described in FIG. 1. At 32 and 45 days post challenge/vaccination, (A) lung-resident AgExp CD4 T cells and (B) lung-resident AgExp CD8 T cells were characterized for their expression of CD69 and CD103. Total numbers of (C) lung-resident memory CD4 T cells and (D) lung-resident memory CD8 T cells were determined. Error bars mean±s.e.m. Data are two pooled experiments with n=8 mice/group. *P<0.05, P<0.01, **P<0.0001 (One-way ANOVA with Tukey's multiple comparisons test).
Figure 18:
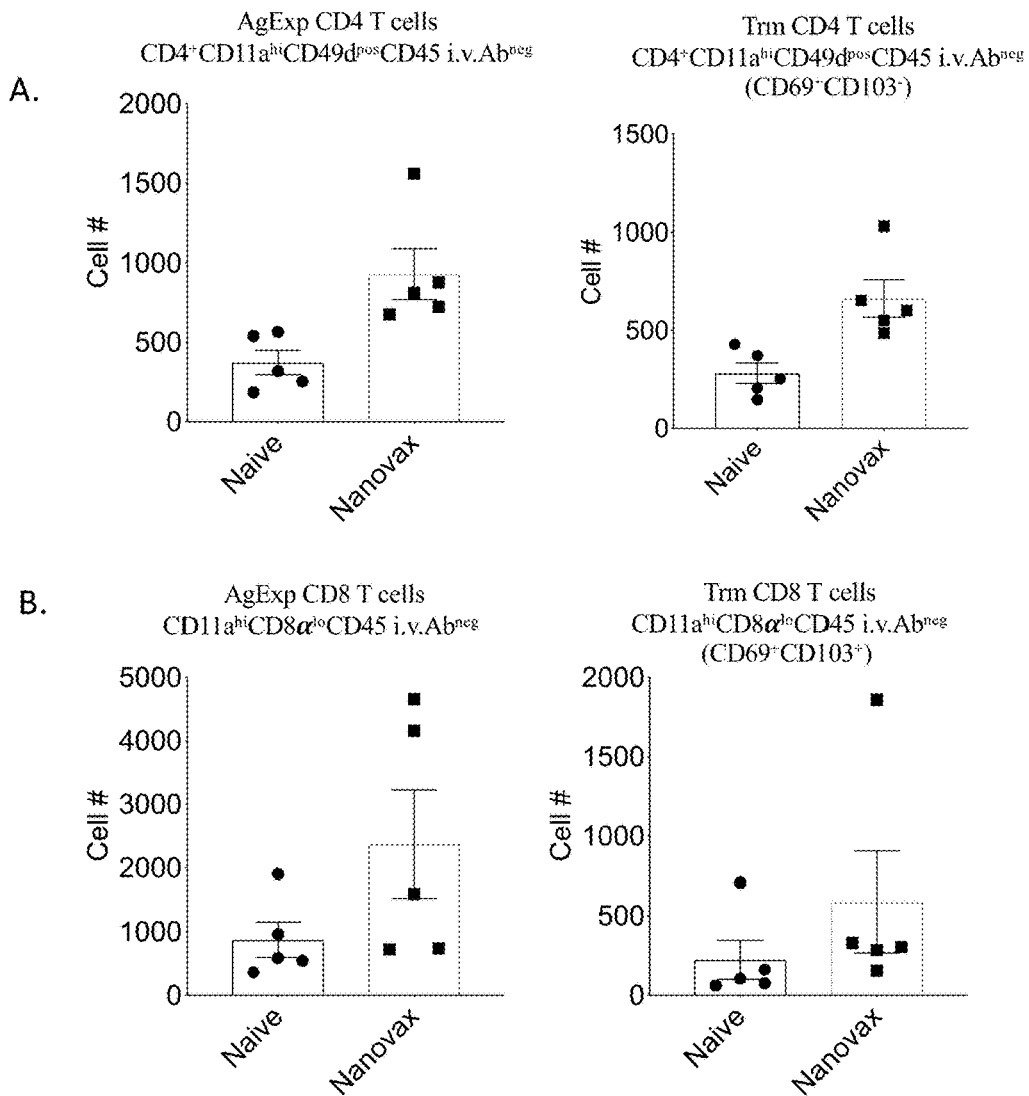
FIG. 18 illustrates IAV-specific lung-resident CD4 and CD8 memory T cell responses induced following IAV-nanovax vaccination are sustained for at least 100 days. C57BL/6 mice were vaccinated with IAV-Nanovax or left unvaccinated (naive). At day 100 post vaccination lungs were harvested and stained for expression of CD4, CD8, CD11a, CD49d, CD69, and CD103. Three minutes prior to the harvest of the tissue, the mice were administered ant-CD45 mAb to identify those cells within the blood vs those within the tissues. Shown are the number of (A) total lung-resident AgExp CD4 T cells (CD11a$^{hi}$CD49d$^{pos}$CD45 i.v.Ab$^{neg}$) and lung-resident AgExp Trm CD4 T cells (CD4$^+$ CD11a$^{hi}$CD49d$^{pos}$CD45 i.v.Ab$^{neg}$CD69$^+$CD103$^-$) or (B) total lung-resident AgExp CD8 T cells (CD11a$^{hi}$CD8α$^{lo}$CD45 i.v.Ab$^{neg}$) and lung-resident AgExp Trm CD8 T cells (CD11a$^{hi}$CD8α$^{lo}$CD45 i.v.Ab$^{neg}$CD69$^+$CD103$^+$).
Figure 19:
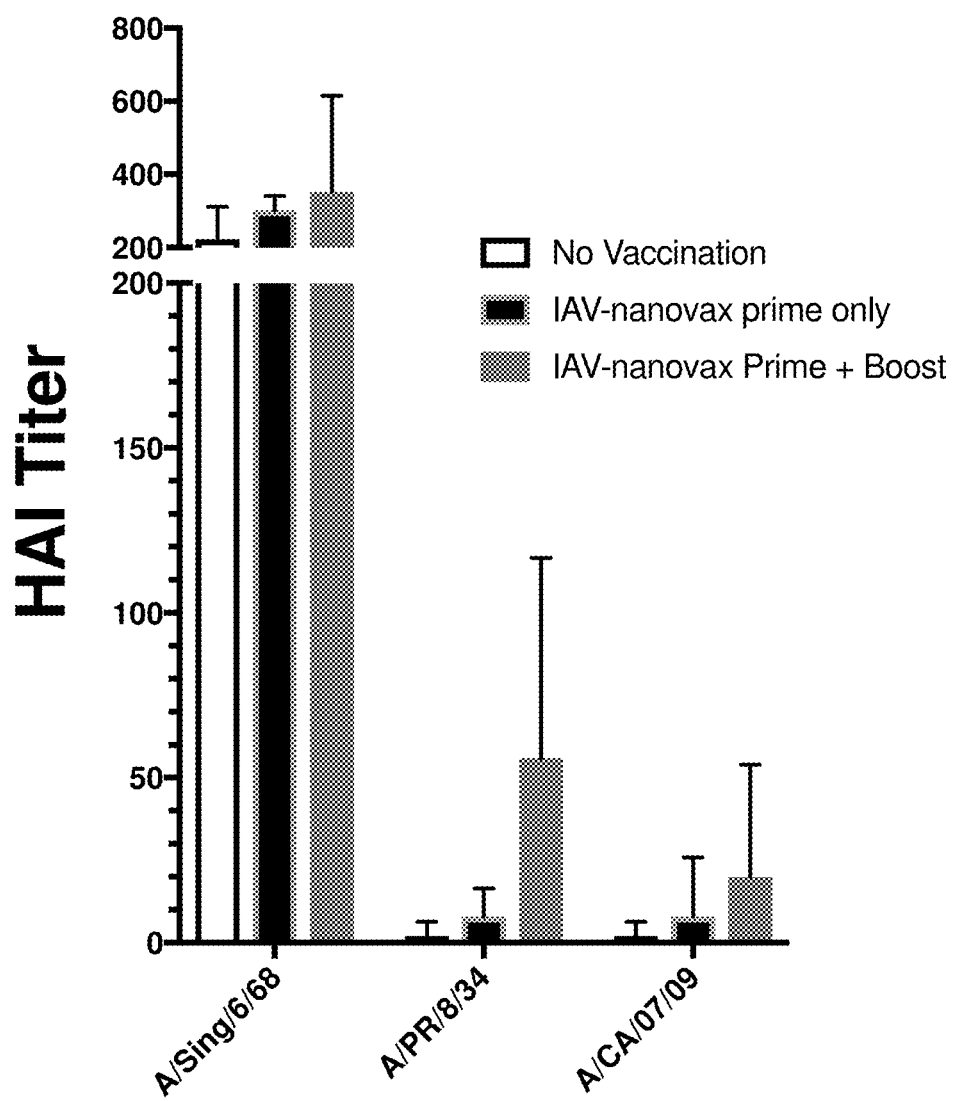
FIG. 19 illustrates IAV-nanovax induces antibody responses in pre-immune populations. Ferrets were made pre-immune via infection with an A/Singapore/6/68 (H1N1) virus. 70 days later some of the ferrets were administered IAV-nanovax [formulation contained a ferret reactive CpG sequence and HA and NP proteins from A/PR/8/34 (H1N1)]. 35 days after the initial vaccination a group of the vaccinated ferrets was boosted with another i.n. administration of the IAV-nanovax. While control pre-immune ferrets that were not vaccinated showed the expected immunity (Ab) to A/Singapore/6/68 they did not have protective antibody titers against A/PR/8/34 or A/CA/09 (H1N1). Pre-immune ferrets vaccinated with IAV-nanovax showed protective titers against both A/Singapore and A/PR/8/34 at day 121 of the experiment. Additionally, these ferrets showed some antibody reactivity to A/CA/09. These positive results are important since the ferret is a key pre-clinical model and humans are inherently pre-immune to a variety of influenza viruses. Thus, these results show that IAV-nanovax works in pre-immune populations. Data was generated through the non-clinical and pre-clinical services program offered by the National Institute of Allergy and Infectious Diseases.
Figure 20:
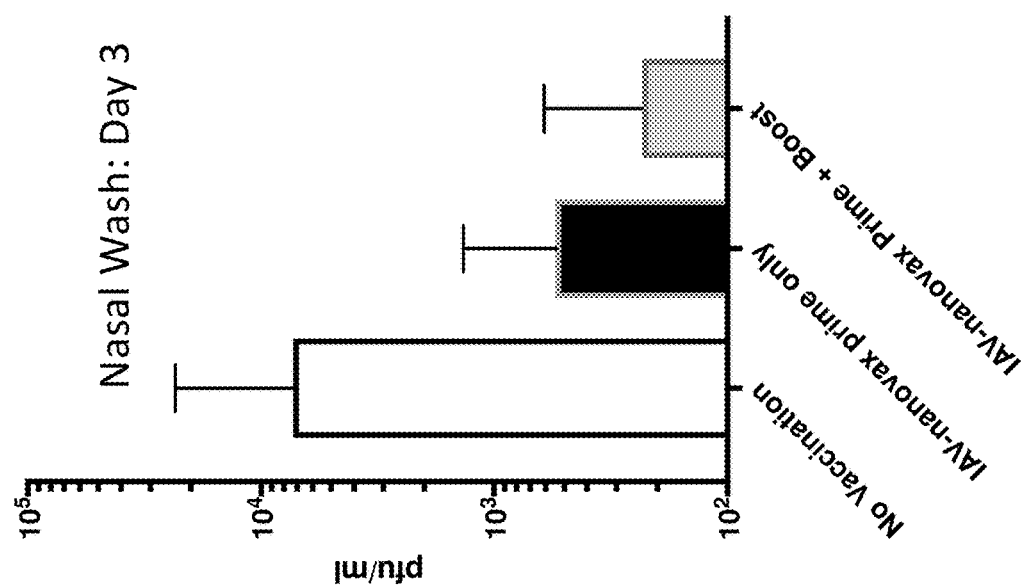
FIG. 20 illustrates IAV-nanovax induces protection in pre-immune populations. Ferrets were made pre-immune via infection with an A/Singapore/6/68 (H1N1) virus. 70 days later some ferrets were administered IAV-nanovax containing a ferret reactive CpG sequence and HA and NP proteins from A/PR/8/34 (H1N1). 35 days after the initial vaccination a group of the vaccinated ferrets was boosted with another i.n. administration of the IAV-nanovax. On day 126 of the experiment the ferrets were challenged with A/CA/07/09 ($10^6$ pfu). While control pre-immune ferrets lost weight and shed virus, those vaccinated with IAV-nanovax shed less virus and lost less weight. These positive results are important since the ferret is a key pre-clinical model and humans are inherently pre-immune to a variety of influenza viruses. Thus, these results show that IAV-nanovax works in pre-immune populations. Data was generated through the non-clinical and pre-clinical services program offered by the National Institute of Allergy and Infectious Diseases.
Figure 20:
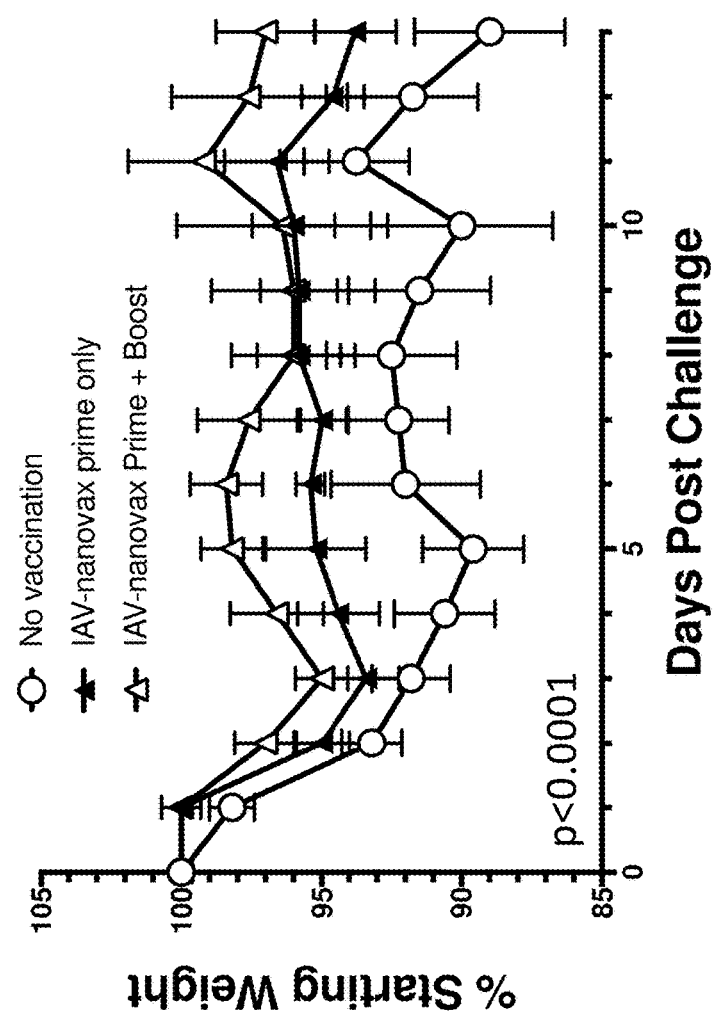
Figure 21:
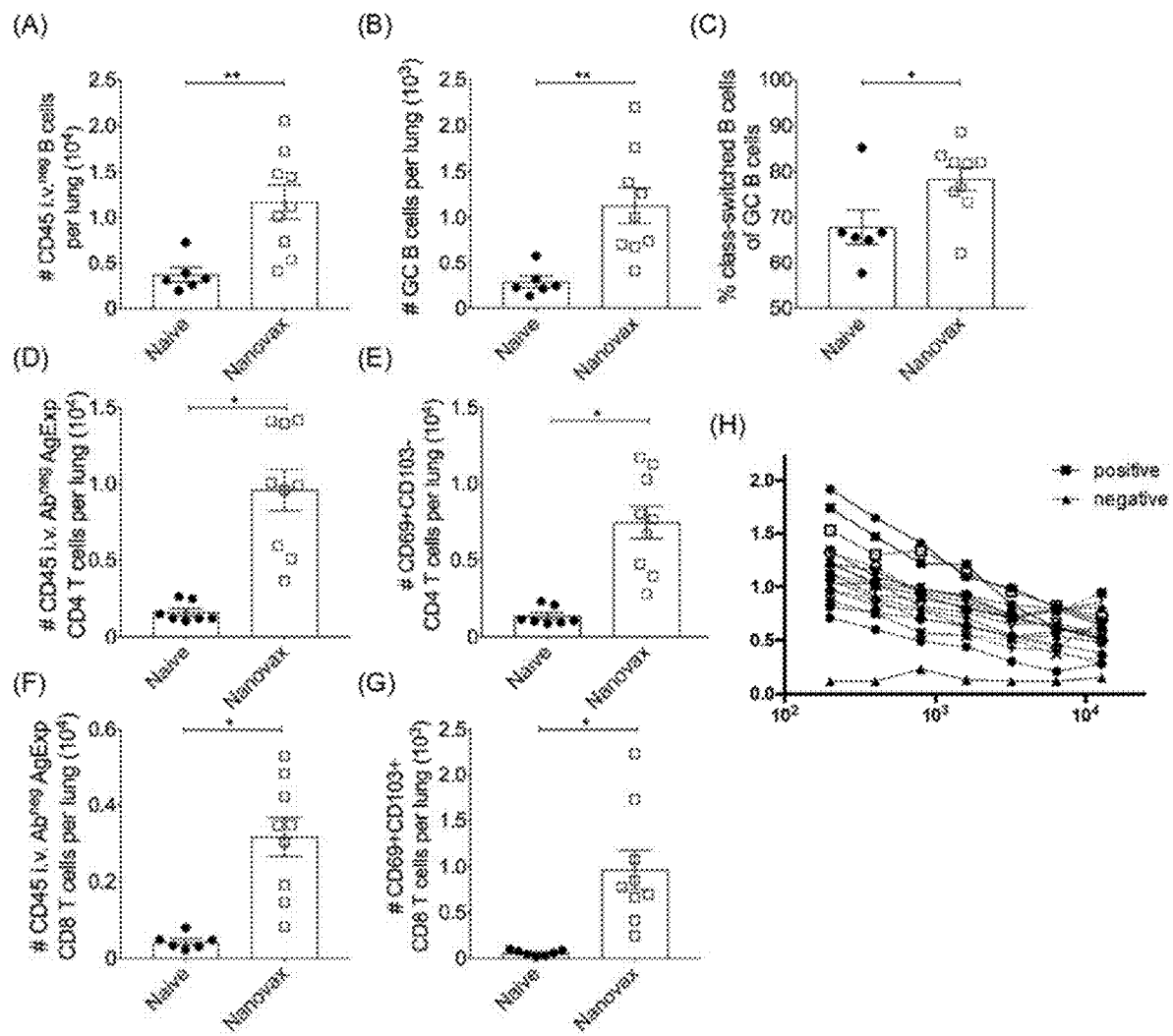
FIG. 21 illustrates the immune response of outbred mice following IAV-nanovax vaccination. Outbred Swiss Webster mice received a prime+boost i.n. vaccination with IAV-nanovax without free protein or were left unvaccinated (naïve). At 45 days following vaccination (A) lung-resident B cells, (B) germinal center (GC) B cells, (C) class-switched GC B cells, (D) lung-resident CD4 T cells, (F) lung-resident CD8 T cells, and (E, G) tissue-resident memory T cells were enumerated within the lungs. Error bars mean±s.e.m. Data are representative of one independent with n=7-9 mice/group. *P<0.05, **P<0.01 (Two-tailed t test). On day 32 post vaccination, mice were bled and the IAV-specific antibody levels in the serum determined by ELISA. Line with filled triangles=negative control serum from naïve mice. Solid line with filled squares=positive control serum. The remaining lines show the individual IAV-specific antibody responses for the vaccinated Swiss-Webster mice. Overall these positive results demonstrate that IAV-nanovax induces tissue resident memory CD4 and CD8 T cells and GC B cell responses in the lungs and IAV-specific antibody in the serum of outbred animals. Importantly, these outbred mice represent the genetic diversity found in humans.
Figure 22:
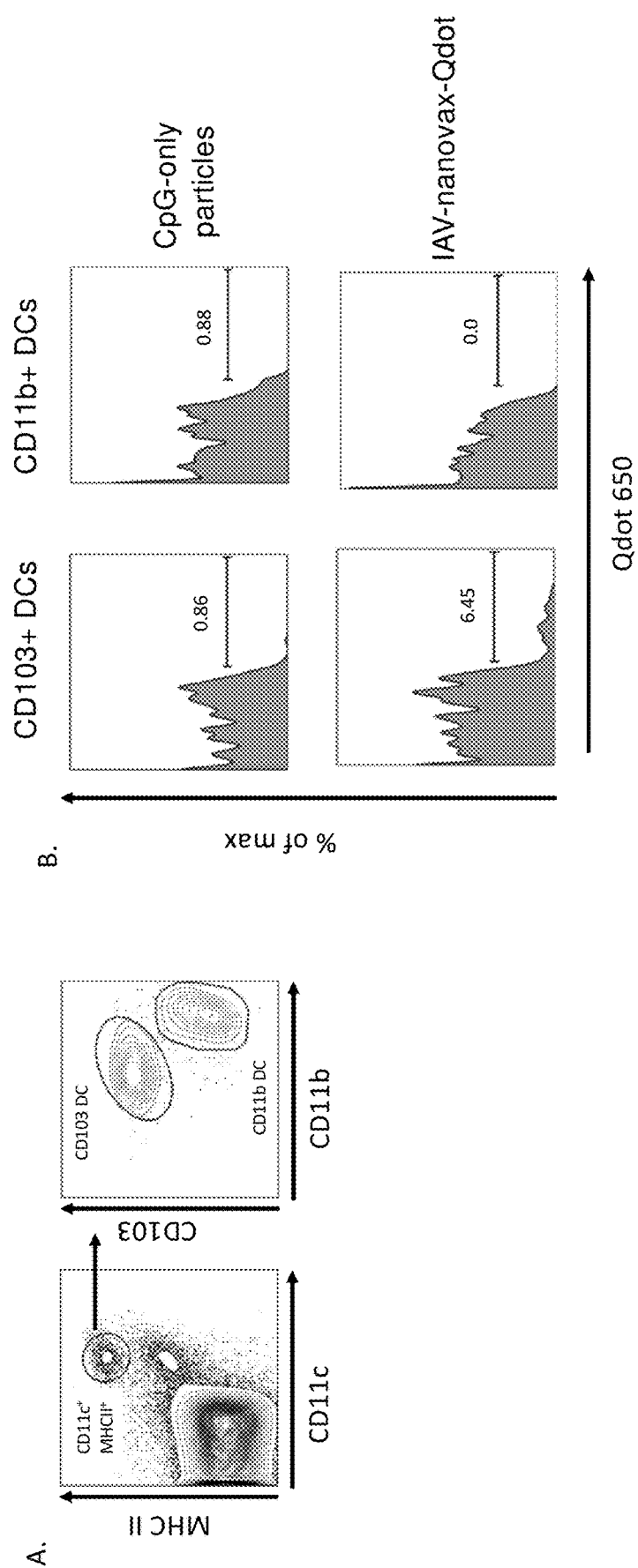
FIG. 22 illustrates that migratory CD103$^+$ lung dendritic cells (DC) carry IAV-nanovax from the lungs to the lung draining lymph nodes. C57BL/6 mice were vaccinated with Nanovax-Qdot, or CpG only nanoparticles (i.e. no Qdot or IAV proteins). At 30 hours post vaccination, the lung draining lymph nodes were isolated and cells analyzed for presence of the Qdot nanoparticles. (A) Gating strategy for CD45$^+$B220$^-$ cells to identify CD103+ and CD11b+DC within the lymph nodes. (B) Quantification of the fraction of the indicated DC containing Qdot+-Nanovax. These results demonstrate that only CD103+ lung DC that have migrated from the lungs to the lung draining lymph nodes contain Qdot+IAV-nanovax at 30 hours post vaccination. Qdot staining is not observed when CpG only nanoparticles, which lack the Qdot, are used demonstrating the specificity of the assay. Further the lack of Qdot+CD11b+DC following Nanovax-Qdot vaccination suggests that the IAV-nanovax does not drain directly to the lymph nodes as such drainage would make it accessible to uptake by CD11b+DC within the lymph nodes. Finally, as a fraction of the CD11b+DC present in the lymph nodes have recently migrated from the lung interstitium to the lymph nodes, the presence of Qdot only in CD103+DC suggest that it may be selectively carried to the lymph nodes by the CD103+DC which are known to be initially positioned within the airways of the lung.

Previous studies have shown that the maintenance of Trm T cells within lung niches is influenced by the presence and longevity of antigen depots. Following IAV-nanovax vaccination, we observed the presence of both CD4 and CD8 Trm cells within the lungs on day 32 and 45 post vaccination at numbers similar to those observed in an IAV infected lung (FIG. 4). Preliminary studies also suggest that CD4 and CD8 Trm responses are present in the lungs out to at least day 100 (FIG. 18). Our prior studies have shown nanoparticles persist within the lungs for ≥14 days and the continual release of antigen from nanoparticles placed into other tissues ≥30 days following vaccination. Overall this suggests that IAV-nanovax may act as an antigen depot, similar to what is observed during IAV infections, and that this may contribute to the upkeep of lung-resident memory T cells.

In conclusion, we have shown that an i.n. inoculation with a polyanhydride nanovaccine encapsulating IAV proteins (IAV-nanovax) provides protection against homologous and heterologous IAV infections. This protection was associated with the induction of GC B cells in the lungs, robust IAV-specific antibody responses both systemically and locally, and IAV-specific CD4 and CD8 T cell responses within the lungs. Further, this report demonstrates for the first time that i.n. vaccination with polyanhydride nanoparticles can induce tissue-resident memory CD4 and CD8 T cells, confer protection against a heterologous virus challenge, and protect against infection in outbred populations. Altogether these findings highlight the potential of utilizing this nanovaccine platform for vaccine delivery in order to induce both systemic and localized adaptive immunity and provide protection against IAV infections.

Example 2. IAV-Nanovax Induces Influenza Specific Memory CD4 and CD8 T Cell Response in the Nasal Passage and Lungs FIG. 12 and FIG. 13 illustrate the presence of tissue-resident antigen CD4 T cells, CD8 T cells 45 days post initial vaccination (i.n. challenge with the IAV-nanovax) using surface marker expression algorithms and tissue localization techniques. Within the nasal tissue-resident antigen-reactive T cell population, surface marker expression further documented the presence of memory CD4 T cells and CD8 T cells. Multiple reports in the literature underscore the need for tissue resident memory T cells (referred to as Trm) to establish long-term protection against influenza infection.

The same surface marker expression analysis has been used to document the presence of tissue-resident antigen-reactive CD4 T cells and CD8 T cells in the nasal passages 45 days after initial i.n. challenge with the IAV-nanovax. Within the nasal tissue-resident antigen-reactive T cell population, surface marker expression clearly documented the presence of memory T cells.

Example 3. IAV-Nanovax Administration Induces Both a Local (i.e., Lung) as Well as Systemic (Spleen) Immune Response but that i.n. Administration is Necessary to Drive a Robust Adaptive Immune Response within the Lungs FIG. 14 illustrates the presence of antigen reactive B cells (germinal center B cells), CD4 T cells and CD8 T cells 45 days after either i.n. or subcutaneous (s.c.) administration of the IAV-nanovax, these antigen reactive cells were only found in the lung after i.n. challenge. Antigen reactive cells were found in the spleen (indicative of system distribution) after both i.n. and s.c. challenge (with more cells found in the spleen after s.c., as expected). The figure further demonstrates that the presence of antigen-reactive B cells, CD4 T cells and CD8 T cells in the spleen after i.n. vaccination with the IAV-nanovax.

Example 4. 2X-Nanovax Confers Protection Against Homologous and Heterologous Viruses Using a Single i.n. Vaccination without a Boost FIG. 15 and FIG. 16 illustrate the induction of adaptive immunity and protection against influenza challenge (homologous and heterologous viruses) after a single i.n. administration of an IAV-nanovax formulation using a "2X" formulation. Specifically, particles were loaded using 2.5× protein payload (although the same amount of CpG adjuvant was used). This data demonstrates that a single dose may provide systemic protection against Influenza rather than the need for a prime-boost.

Example 5. No Immunity is Observed when Mice are Vaccinated with Nanoparticles that Contain the CpG but Lack the Influenza Immunogenic Proteins FIG. 17 illustrates that the influenza immunogenic protein payload is necessary to confer protection. Specifically, nanoparticles loaded with influenza target proteins+the CpG adjuvant confer protection whereas nanoparticles loaded with the CpG adjuvant alone do not.

Example 6. Tissue Resident Memory CD4 and CD8 T Cells are Sustained in the Lungs to at Least 100 Days Post IAV-Nanovax Administration FIG. 18 illustrates the presence of influenza-protective immune T cells in the lung and, importantly, confers protection (FIG. 6) against both homologous and heterologous influenza virus challenge extending to 100 day post initial administration of IAV-nanovax (IAV-nanovax given i.n.).

Example 7. IAV-Nanovax Generates Immunity and Confers Protection in Pre-Immune Populations FIG. 19 and FIG. 20 illustrate the induction of neutralizing Ab and protection in pre-immune outbred ferrets after intranasal (i.n.) administration of IAV-nanovax. Ferrets were made pre-immune via infection with an A/Singapore/6/68 (H1N1) virus. 70 days later some of the ferrets were administered IAV-nanovax [formulation contained a ferret reactive CpG sequence and HA and NP proteins from A/PR/8/34 (H1N1)]. 35 days after the initial vaccination a group of the vaccinated ferrets was boosted with another i.n. administration of the IAV-nanovax. While control pre-immune ferrets that were not vaccinated showed the expected immunity (Ab) to A/Singapore/6/68 they did not have protective titers against A/PR/8/34 or A/CA/09 (H1N1).

Pre-immune ferrets vaccinated with IAV-nanovax showed protective titers against both A/Singapore and A/PR/8/34 at day 121 of the experiment. Additionally, these ferrets showed some antibody reactivity to A/CA/09 and shed less virus and lost less weight upon subsequent challenge with A/CA/09 virus. These positive results are important since the ferret is a key pre-clinical model and humans are inherently pre-immune to a variety of influenza viruses.

Example 8. IAV-Nanovax Induces Tissue Resident Memory CD4 and CD8 T Cells and GC B Cell Responses in the Lungs and IAV-Specific Antibody in the Serum of Outbred Animals FIG. 21 illustrates the induction of full adaptive immunity (antigen-reactive B cells, Ab, CD4 T cells, CD8 T cells) and protection against influenza challenge (both homologous and heterologous, see FIG. 7) in outbred Swiss-Webster mice that are similar to the genetic diversity of humans after i.n. IAV-nanovax administration.

Example 9. CD103+ Lung DC Migrating from the Lungs to the Lung Draining Lymph Nodes Contain Qdot+IAV-Nanovax at 30 Hours Post Vaccination FIG. 22 illustrates the use of nanoparticles loaded with highly fluorescent quantum dots (Qdots) we have shown the nanoparticles to be taken up by dendritic cells (DCs) and other antigen presenting cells (APCs) in the lungs, and within DCs that have migrated from the lungs into the lung draining lymph nodes. Qdot containing particles are not found in DCs in lymph nodes that do not drain the lungs (control experiment).

Further the lack of Qdot+CD11b+DC following Nanovax-Qdot vaccination indicates that the IAV-nanovax does not drain directly to the lymph nodes as such drainage would make it accessible to uptake by CD11b+DC within the lymph nodes. Finally, as a fraction of the CD11b+DC present in the lymph nodes have recently migrated from the lung interstitium to the lymph nodes, the presence of Qdot only in CD103+DC suggest that it may be selectively carried to the lymph nodes by the CD103+DC which are known to be initially positioned within the airways of the lung. These findings indicate that the IAV-nanovax easily travels to the lower airway (lung) after i.n. administration and is transported via DC through the lymphatics to the draining lymph nodes to induce local and systemic immunity.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An immunogenic composition comprising:

one or more polyanhydride copolymers forming a biodegradable first polyanhydride nanoparticle, the copolymers including 1,8-bis(p-carboxyphenoxy)-3,6-dioxaoctane (CPTEG) and 1,6-bis(p-carboxyphenoxy) hexane (CPH) in a ratio of about 20:80;

an adjuvant other than CPTEG, CPH, or combinations thereof;

one or more immunogenic proteins of an Influenza Virus, the influenza Virus selected from the group consisting of Influenza A Virus, Influenza B Virus, Influenza C Virus, and Influenza D Virus wherein each of the adjuvant and the one or more immunogenic proteins are entrapped within the nanoparticle; and an excipient.

2. The immunogenic composition of claim 1 further comprising at least a second biodegradable polyanhydride nanoparticle formed of one or more polyanhydride copolymers, the copolymers including CPTEG and CPH in a ratio of about 20:80; a second immunogenic protein of an Influenza Virus and an adjuvant within an interior of the second nanoparticle, the second immunogenic protein being different than the immunogenic protein.

3. The immunogenic composition of claim 1, wherein the immunogenic proteins include one or more subtypes of the Influenza A virus selected from the group consisting of H1, H2, H3, H5, H7, and H9.

4. The immunogenic composition of claim 1, wherein the immunogenic proteins include one or more of Hemagglutinin (HA), Neuraminidase (NA), Nucleocapsid Protein (NP), Matrix Protein 1 (M1), Matrix Protein 2 (M2), Polymerase Basic Protein 1 (PB1), Polymerase Basic Protein 2 (PB2), Polymerase Acidic Protein (PA), Nonstructural Proteins 1 (NS1), Nonstructural Proteins 2/Nuclear Export Protein (NS2/NEP), Polymerase Basic Protein 1 Segment Second Proteins (PB1-F2), Influenza B Virus Membrane Protein (BM2), Influenza B Virus Membrane Protein (NB), Influenza A Virus Segment 2 Alternative Splicing Protein (M42), Influenza A Virus Segment 1 Alternative Splicing Protein (PB2-S1), Influenza A Virus Segment 2 Alternative Initiation Protein (N40), Influenza A Virus Segment 3 Ribosomal Shift Protein (PA-X), Influenza A Virus Segment 3 Alternative Initiation Protein (PA-N182), Influenza A Virus Segment 3 Alternative Initiation Protein (PA-N155), Influenza C/D Virus Polymerase Complex Protein (P3), Influenza C/D Virus Surface Glycoproteins: Hemagglutinin, Esterase, and Fusion activities (HEF), Influenza C/D Virus Matrix Protein (CM1), or Influenza C/D Virus surface glycoprotein CM2.

5. The immunogenic composition of claim 1, wherein the immunogenic proteins are selected from the group consisting of Influenza A Virus Hemagglutinin (HA) subtypes H1, H2, and H3, Influenza A Virus Neuraminidase (NA) subtypes N1 and N2, Influenza A Virus Nucleocapsid Protein (NP), Influenza A Virus Matrix Protein 1 (M1), Influenza B Virus HA and NA, Influenza A Virus HA subtypes H1 and H3, Influenza A Virus NA subtypes N1 and N2, Influenza A Virus NP, M1, Nonstructural Proteins 1 (NS1), Polymerase Acidic Protein (PA), and Polymerase Basic Protein 1 (PB1), Influenza A Virus HA subtypes H5, H7, and H9, Influenza A Virus NA subtypes N1, N2, N7, and N9, and Influenza A Virus NP and M1.

6. The immunogenic composition of claim 1, further comprising one or more free immunogenic proteins of Influenza Virus proteins in the excipient.

7. The immunogenic composition of claim 1, wherein the adjuvant includes a Toll-Like Receptor (TLR) agonist selected from the group consisting of is TLR5 agonist, a TLR7 agonist, or a TLR9 agonist;

a liposome, a mineral salt, an oil emulsion, a polymer, a polysaccharide, a saponin, CpG oligonucleotide, or a STING activating adjuvant.

8. The immunogenic composition of claim 1 further comprising a second adjuvant in the excipient.

9. An immunogenic composition comprising:

one or more polyanhydride copolymers forming a biodegradable first polyanhydride nanoparticle, the copolymers including 1,8-bis(p-carboxyphenoxy)-3,6-dioxaoctane (CPTEG) and 1,6-bis(p-carboxyphenoxy) hexane (CPH) in a ratio of about 20:80;

an adjuvant;

one or more immunogenic proteins of an Influenza Virus, the Influenza Virus selected from the group consisting of Influenza A Virus, Influenza B Virus, Influenza C Virus, and Influenza D Virus wherein each of the adjuvant and the one or more immunogenic proteins are entrapped within the nanoparticle;

a targeting protein comprising an antibody or ligand disposed on at least a portion of a surface of the nanoparticle that targets the nanoparticle to a lung dendritic cell or a lung macrophage cell; and an excipient.

10. The immunogenic composition of claim 9, wherein the antibody or the ligand disposed on the surface of the nanoparticle specifically binds to CLEC9a, Dectin-1, SIRpa, or MERtK.

11. An immunogenic composition comprising:

one or more polyanhydride copolymers forming a biodegradable first polyanhydride nanoparticle, the copolymers including 1,8-bis(p-carboxyphenoxy)-3,6-dioxaoctane (CPTEG) and 1,6-bis(p-carboxyphenoxy) hexane (CPH) in a ratio of about 20:80;

an adjuvant;

one or more immunogenic proteins of an Influenza Virus, the Influenza Virus selected from the group consisting of Influenza A Virus, Influenza B Virus, Influenza C Virus, and Influenza D Virus wherein each of the adjuvant and the one or more immunogenic proteins are entrapped within the nanoparticle; and an excipient; wherein the nanoparticles comprise by weight about 1% HA protein, about 1% NP protein, and about 2% CpG oligonucleotide.

12. A method of inducing an immune response to influenza in a subject comprising administering to the subject an effective amount of the immunogenic composition of claim 1 to induce the immune response.

13. The method of claim 12 further comprising administering to the subject at least a second biodegradable polyanhydride nanoparticle formed of one or more polyanhydride copolymers, the copolymers including CPTEG and CPH in a ratio of about 20:80; a second immunogenic protein of an Influenza Virus and an adjuvant within an interior of the second nanoparticle, the second immunogenic protein being different than the immunogenic protein.

14. The method of claim 12, wherein the immunogenic proteins comprise one or more subtypes of the Influenza A virus selected from the group consisting of H1, H2, H3, H5, and H7.

15. The method of claim 12, wherein the adjuvant comprises a Toll-Like Receptor (TLR) agonist selected from the group consisting of is TLR5 agonist, a TLR7 agonist, or a TLR9 agonist;

a liposome, a mineral salt, an oil emulsion, a polymer, a polysaccharide, a saponin, CpG oligonucleotide, or a STING activating adjuvant.

16. The method of claim 12, wherein the nanoparticle further comprises a targeting protein disposed on at least a portion of a surface of the nanoparticle that targets the nanoparticle to a specific cell type.

17. The method of claim 12, wherein the nanoparticles comprise by weight about 2.5% HA, about 2.5% NP, and about 2% CpG oligonucleotide.

18. The method of claim 17, wherein the nanoparticles comprise by weight about 1% HA, about 1% NP, and about 2% CpG oligonucleotide.

19. The method of claim 12, wherein the administering comprises intranasal administration and an optional subsequent intramuscular or subcutaneous administration.

20. The method of claim 12, wherein the immune response comprises both a local immune response and a systemic immune response.

* * * * *